(12) United States Patent
Cassingham et al.

(10) Patent No.: US 12,319,974 B2
(45) Date of Patent: Jun. 3, 2025

(54) USE OF REACTIVE CROSS-LINKING AGENTS FOR PROTEIN-CONTAINING SUBSTRATES AND PROCESSES FOR TANNING AND DYEING OF LEATHER

(71) Applicant: Archroma (Switzerland) GmbH, Pratteln (CH)

(72) Inventors: Daryl Miles Cassingham, Dorset (GB); Laszlo Fekete, Basel (CH); Michael Nicollet, Basel (CH); Jean Christophe Graciet, Basel (CH); Georg Roentgen, Basel (CH)

(73) Assignee: Archroma (Switzerland) GmbH, Pratteln (CH)

( * ) Notice: Subject to any disclaimer, the term of this patent is extended or adjusted under 35 U.S.C. 154(b) by 31 days.

(21) Appl. No.: 18/268,372

(22) PCT Filed: Dec. 21, 2021

(86) PCT No.: PCT/EP2021/087045
§ 371 (c)(1),
(2) Date: Jun. 20, 2023

(87) PCT Pub. No.: WO2022/136403
PCT Pub. Date: Jun. 30, 2022

(65) Prior Publication Data
US 2024/0052438 A1  Feb. 15, 2024

(30) Foreign Application Priority Data
Dec. 23, 2020  (EP) .................................... 20217159

(51) Int. Cl.
*C14C 3/00* (2006.01)
*C07D 251/50* (2006.01)
(Continued)

(52) U.S. Cl.
CPC .............. *C14C 3/26* (2013.01); *C07D 251/50* (2013.01); *D06P 1/384* (2013.01); *D06P 1/628* (2013.01)

(58) Field of Classification Search
CPC .... C14C 3/26; C14C 3/28; C14C 3/08; C07D 251/50; D06P 1/384; D06P 1/628; D06P 1/645; D06P 3/3286
(Continued)

(56) References Cited

U.S. PATENT DOCUMENTS 6,120,562 A    9/2000  Patsch et al.
2013/0227799 A1    9/2013  Reineking et al.

FOREIGN PATENT DOCUMENTS

CN    104672160 A    6/2015
EP    0175225 A2 *  3/1986    ........... C07D 251/70
(Continued)

OTHER PUBLICATIONS

STIC Search Report dated Sep. 16, 2024.*
(Continued)

*Primary Examiner* — Eisa B Elhilo
(74) *Attorney, Agent, or Firm* — Christensen, Fonder, Dardi PLLC; Elizabeth A. Gallo; Peter S. Dardi

(57) ABSTRACT

The present invention relates to the use of reactive colourless and metal-free protein cross-linking agents for the cross-linking (tanning) of protein-containing substrates, said agents are environmentally friendly and give an improved fixation yield, a long-term cross-linking (tanning) stability and good washing off properties. The present invention further relates to processes for the cross-linking (tanning) of protein-containing substrates thereby creating an environmentally friendly process which minimizes the use of chemicals and further improves the quality and efficiency of the tanning and dyeing process.

(Continued)

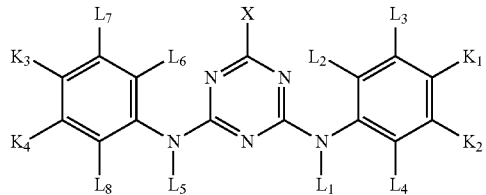

17 Claims, 5 Drawing Sheets

(51) Int. Cl.
*C14C 3/26* (2006.01)
*D06P 1/384* (2006.01)
*D06P 1/62* (2006.01)

(58) Field of Classification Search
USPC .............................................................. 8/426
See application file for complete search history.

(56) References Cited

FOREIGN PATENT DOCUMENTS

WO  2010130311 A1  11/2010
WO  2019158341 A1  8/2019

OTHER PUBLICATIONS

Lewis D M et al., "Improved Fixation of Dyes on Polyamide Fibres. Part 3: Using 2-Chloro-4,6-di (aminobenzene-4@?-vinylsulphone)-s-Triazine [XLC-VS] as an After-Treatment of Nucleophilic Aminoalkyl Dyes", Dyes and Pigments, Elsevier Applied Science Publishers Barking, GB, vol. {0} 30, No. {0} 4, Apr. 1, 1996 (Apr. 1, 1996), p. 301-314. Abstract only.

* cited by examiner

USE OF REACTIVE CROSS-LINKING AGENTS FOR PROTEIN-CONTAINING SUBSTRATES AND PROCESSES FOR TANNING AND DYEING OF LEATHER

This application is the National Phase of International Application PCT/EP2021/087045 filed Dec. 21, 2021 which designated the U.S. and which claims priority to EP 20217159.1 filed Dec. 23, 2020. The noted application is incorporated herein by reference.

FIELD OF INVENTION

The present invention relates to the use of reactive colourless and metal-free protein cross-linking agents of protein-containing substrates, said agents are environmentally friendly and give an improved fixation yield, a long-term cross-linking (tanning) stability and good washing off properties.

The present invention further relates to processes for the cross-linking (tanning) of protein-containing substrates thereby creating an environmentally friendly process which minimizes the use of chemicals and further improves the quality and efficiency of the tanning and dyeing process over time.

BACKGROUND OF THE INVENTION

The manufacturing process of leather has an environmental impact, especially because not all the chemicals used in the manufacturing process end up in the leather but are released into the environment. The gauge of a leather's eco friendliness is measured by the absence of certain restricted chemicals, such as chrome VI and formaldehyde or the method of tannage. This push originated from the automotive sector, but more recently by environmental pressure groups, eco labels, high street retailers or those seeking to gain competitive advantage through product positioning. The so called ZDHC Programme was established by brands to advance towards zero discharge of hazardous chemicals in the textile, leather and footwear value chain.

The history of leather started with primitive man hunting wild animals for food. Hides and skins obtained as a by-product from the dead animal carcass were used as crude-forms of shelter, clothing and footwear. A method of preservation was needed, because the hides, pelts and skins rapidly putrefied and decomposed. However, the early preservation methods, such as drying the skins, had only a limited preserving and softening action.

The whole purpose of tanning is to crosslink and stabilize the protein matrix of collagen in order—but not limited—to prevent putrefaction and hence decomposition, to generate a degree of softness, to make sure hydrothermal denaturation is occurring at higher temperatures, to give enhanced resistance to microorganisms, etc. A decent tannage is also largely irreversible. Another property is that the leather can be much more resistant to shrinkage when subjected to moist heat, compared to raw or untanned hide or skin, that is tanning increases the hydrothermal stability, commonly referred to as the hydrothermal shrinkage temperature.

A primary requirement for the quality of tanning is determined by measuring the "hydrothermal stability", more commonly referred to as the "shrinkage temperature". Whenever hides, skins and leathers are gradually heated in water, they reach a temperature at which they are subject to sudden, irreversible shrinkage. Raw hides or skins shrink very easily at temperatures of about 60° C. (at neutral pH values), whereas tanning increases the point at which shrinkage occurs to higher temperatures. This increased resistance to moist heat is an important requirement for leather, for example, when making a wide range of types of footwear in which the leather is subjected to moisture and high temperatures as part of the manufacturing process.

Nowadays a variety of different processes involving different tanning agents are used to tan leather, such as chrome tanning, vegetable tanning and aldehyde tanning. Different types of tanning (pre-tanning, main-tanning and re-tanning) produce different physical properties, including levels of resistance to moist heat in the resulting leather.

None of the above indicated tanning technologies commonly applied offers a full environmental advantage over the others when considering all the key criteria that characterise the impact on the environment of these technologies. The aldehyde tanned leathers meet the needs of the automotive sector and appear to fit a niche within children's products that need to comply with EN71/3, but they can have handling, effluent treatment and higher energy and chemical consumption issues. Moreover, aldehyde tanning is now also coming under increased legislative scrutiny. On the other hand, there is a high request from industry for chrome-free and metal-free tanning agents.

Non-metallic tanning typically creates a very anionic leather. Exhaustion and fixation of other agents used in leather processing, such as other tanning agents, syntans, dyes and fat liquors which are all typically anionic as well, becomes more difficult as the number of functional sites on the collagen are used up. This is well known to those who practice the art in the industry, and so it can be difficult to create, for example, a jet black anionic dyeing on metal free leathers as the dye has significantly reduced sites in the collagen matrix to react with.

WO 2010/130311 relates to the use of triazine derivatives for tanning the leather, said derivatives have an aromatic ring bearing a sulfo group able to form ionic bond via the sulfo group and also to form a covalent bond with the collagen of the leather. Therefore, they crosslinked or tanned the proteins of the leather to a less good, tanned leather with a low shrinkage temperature.

A significant part of the environmental impact of leather is in the manufacturing processes, taking it from a hide, pelt or skin to finished leather. In this respect it is the environmental stewardship practice of tanners coupled with chemical selection that should determine how eco friendly a leather is. In accordance with the model adopted by some of the world's leading brands that have been working on these issues, the following areas of leather manufacture that have the most significant potential impact can be identified: management of restricted substances, energy consumption, air emissions, waste management (hazardous and non-hazardous), water consumption, control of manufacturing processes, effluent treatment, chrome management and traceability of material.

WO2019/158341 relates to a process for the simultaneous tanning and dyeing of collagen containing fibrous material such as leather by combining two steps of leather production, tanning and dyeing, into a single step, thereby using a reactive dye having protein fiber reactive radicals thus, preserving resources and reducing the environmental impact. Using said reactive dye it will be possible to complete the tanning and dyeing simultaneously but it requires rather high amounts of reactive dye and it will not be possible to create either a non-coloured leather nor a leather that requires either a pastel or medium depth of shade.

There is hence still room to further improve the tanning process in an environmental way and develop metal-free tanning agents which avoid the use of restricted substances, do not impose colour and/or require a smaller amount of dye(s) during the dyeing process.

AIM OF THE INVENTION

It is the goal of the invention to develop reactive cross-linking agents for protein-containing substrates such as leather which are environmentally friendly, give an improved fixation yield, a long-term cross-linking (tanning) stability and good washing off properties of the unfixed cross-linking agent. Said reactive cross-linking (tanning) agents should also assist more in particular the high quality demands in terms of colour strength and fastness, migration stability, to specifically mention fastness to rubbing, wet and perspiration fastness and migration fastness.

It is a further goal of the invention to reduce the amount of chemicals required to perform the cross-linking (tanning) and dyeing process of protein-containing substrates such as leather. Ultimately, the reactive cross-linking agent makes it possible to have a synergistic effect on the colouring when used in combination with a reactive dye and gives more flexibility towards creating more easily different shades of colours, especially creating either a non-colored leather or a leather that requires either a pastel or medium depth of shade.

It is a further goal to perform tanning and dyeing in one step by applying a colourless reactive cross-linking agent in combination with a reactive dye such that simultaneous tanning and dyeing can be achieved in a single step thereby using more effectively the available protein reactive sites on the protein-containing substrates.

DEFINITIONS AND TERMS

In the context of the present invention the following terms have the following meaning:

1) In the context of the present invention "collagen containing fibrous material" is to be understood a pelt, hide or skin with its original fibrous structure more or less intact, including split from animal hide, pelt or skin, for example, the underside of the animal hide, pelt or skin to manufacture suede leather. Furthermore, it includes collagen material capable of forming fibers created through reforming collagen or created through an extrusion or spinning process, for example, by taking waste/poor quality collagen, or through means of recombinant collagen generation providing a non-animal derived source, for example, genetically modified yeasts or transgenic tobacco plants, solubilising and reforming into materials and fibers, in its untanned state, that is before tanning. Beside a pelt, hide or skin this term is also meant to include products made from any suitable source of collagen whether they be wasted and shavings generated in the production of leather, or from natural or synthetic sources of collagen. For avoidance of doubt, a collagen containing fibrous material is to be considered as a "protein-based substrate" according to the present invention.

2) In the context of the present invention "protein-based substrate" is to be understood as a substrate based upon natural or synthetically engineered proteins of collagen, gelatin, fibroin, elastin and soy (soyabean) having at least amine functionality and optionally OH functionality.

3) In the context of the current invention, "Hydrothermal stability" is tested by a Shrinkage tester according to method ISO 3380:2015 and tested to irreversible shrinkage. Alternatively, Differential Scanning Calorimetry (DSC) can be used to determine hydrothermal stability, typically utilising heating rates of 5-10° C. per minute in sealed aluminium pans detecting the endothermic peak of the denaturation point and assessing for the 'onset' temperature.

4) In the context of the current invention, "Colour Fastness to Water" and "Perspiration" are tested in accordance with SLF 412 (IUF 421 as included in test method EN ISO 11642) and SLF 426 (IUF 426 as included in test method EN ISO 11641), respectively.

5) In the context of the current invention, "tanning" is the process of treating a collagen containing substrate, both natural and man-made (synthetically engineered) collagen containing substrates, in particular but not limited to skins and hides of animals to produce leather. Tanning according to this invention makes use of at least one reactive (tanning) agent which effectively forms at least a bivalent covalent linkage between the amine (e.g. Lysine and Ornithine terminal amine, Histidine amine, Hydroxylysine amine, etc) and possibly hydroxyl (e.g. Serine or Tyrosine hydroxyl) groups on the collagen containing substrates and permanently modifies the structure of said substrate making it more durable and less susceptible to decomposition and suitable for co-application with dyes.

6) The term "Tanning Agent(s)", "Reactive Tanning Agent(s)" and "Reactive Cross-linking agents" refer in this invention to at least one reactive (tanning/cross-linking) agent which effectively forms at least a (bivalent) covalent linkage between the amine (e.g. Lysine and Ornithine terminal amine, Histidine amine, Hydroxylysine amine, etc) and possibly hydroxyl (e.g. Serine or Tyrosine hydroxyl) groups on the protein-based substrate/collagen containing substrate and permanently alters the structure of said substrate. In some cases the collagen containing substrates have carboxyl groups which in an intermediate way create reactive species that may react with the reactive cross-linking (tanning) agent of the invention either in a permanent or semi-permanent way. In case of leather processing, reactive cross-linking agents are typically referred to as "tanning agents".

7) The term 'Beamhouse Processing' refers to a series of either chemical or mechanical process steps to treat the collagen containing substrates according to the invention (in particular but not limited skins and hides of animals) prior to the tanning and potentially in conjunction with colouring agents (dyes). The beamhouse processing might include soaking, fleshing, liming, unhairing, deliming and bating, for example scraping away all hair, epidermis and non-collagenous matter prior to tanning.

8) The term "Deliming process" and "deliming" refers to the removal of the alkali donor (such as lime) from the collagen containing substrate (pelt, hide or skin) after the traditional liming step in order to reduce the pH of the treated substrate (pelt, hide or skin) after the high pH of a typical liming stage which typically utilises calcium hydroxide as a source of alkali. There are typically three key aspects to 'Deliming':

The pH of the collagen containing substrate (pelt, hide or skin) is reduced to achieve the correct pH for bating enzymes (typically proteolytic types) to optimally work and complete their biochemical reaction. The pH is typically reduced between the pH ranges of 6.5-9.0 depending on the enzyme used.

Removal of the Ca(OH)$_2$ (or other alkali used) associated with the reduction in pH.

Depletion of the collagen containing substrate (pelt, hide or skin), where partial deswelling occurs due to the pH drop (and thus the collagen returns closer to its iso-electric point) and removal of ions, thus reducing the potential for both osmotic and lyotropic swelling.

Deliming processes may use multiple chemical agents (commonly known as deliming agents) to achieve the above requirements. For the current invention it is preferred that any deliming chemistry used avoids the potential to form insoluble calcium salts (e.g. Calcium Carbonate known as 'limeblast') and possibilities of acid swelling. Examples of suitable deliming agents include, but are not limited to, ammonium-free deliming agents such as the use of Carbon Dioxide injection, derivatives of phosphonic acids, weak acidic salts, water (through continued washing), weak acids such as lactic acid, certain strong acids (such as Hydrochloric acid, although extreme caution must be employed in the rate at which it is added), hydroxyl sinks, etc. The common ammonium based deliming salts, e.g. ammonium sulphate, ammonium chloride, etc, are less preferred and preferably avoided in the current invention.

9) The term 'Limed weight', refers to the weight of the collagen containing substrate (e.g. a pelt, hide or skin) prior to the deliming step and is effectively at a point where the collagen containing substrate (pelt, hide or skin) is very swollen with water (so typically the weight of the collagen containing substrate is 20-30% collagen and 70-80% water).

10) The term 'Pickle weight', refers to the weight of the collagen containing substrate (e.g. pelt, hide or skin) in the storage pickle stage where the pelt, hide or skin is typically at a pH ranging from 1.5-2.5 and in a state where there is little, if any, swelling of the structure due to water (so typically the weight of the collagen containing substrate is 40-45% collagen and 55-60% water).

11) The word "average" refers to number average unless indicated otherwise.

12) Unless otherwise expressed, the "weight percentage" (indicated as % wt or wt %) of tanning agent and/or wt % of dye used in the tanning and/or dyeing process refers to the wt % of the tanning agent and/or wt % of the dye used calculated on the total weight of the dry protein-based substrate. In the case of leather, the wt % of tanning agent and/or wt % of dye used in the tanning and/or dyeing process refers to the wt % of the tanning agent and/or wt % of the dye calculated on the total weight of the protein-based substrate in the "limed state" or "pickle state" unless otherwise stated.

DETAILED DESCRIPTION

The present invention discloses the use of reactive protein cross-linking (tanning) agents for the cross-linking (tanning) of protein-based substrates, said agents are colourless and metal-free. As a result, the cross-linking agents according to the invention are environmentally friendly and give an improved fixation yield, a long-term cross-linking (tanning) stability and good washing off properties.

The present invention therefore discloses the use of reactive protein cross-linking (tanning) agents for the cross-linking (tanning) of protein-based substrates having amine and optionally OH functionality, said cross-linking (tanning) agents selected from compounds according to formula [1]:

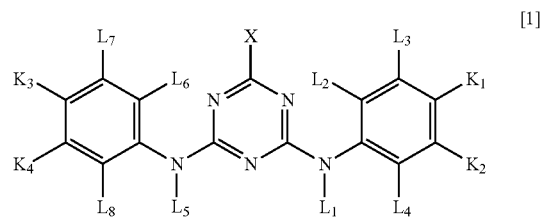

Wherein $L_1$ and $L_5$ are each independently from each other selected from H or C1-C4 alkyl, and $L_2$, $L_3$, $L_4$, $L_6$, $L_7$ and $L_8$ are each independently from each other selected from H, C1-C4 alkyl, $SO_3H$, $OL_{22}$ wherein $L_{22}$ is selected from H or C1-C4 alkyl, and X is selected from Cl, F or nicotinic acid, and $K_1$, $K_2$, $K_3$ and $K_4$ are each independently from each other selected from —H or protein reactive radicals According to embodiments, the protein reactive radicals in the cross-linking (tanning) agents according to the invention (see compounds according to formula [1]) are selected from —$SO_2$—Y,
—NH—$(CH_2)_{2-3}$—$SO_2$—Y,
—NH—CO—$(CH_2)_{2-3}$—$SO_2$—Y,
—NH—$(CH_2)_2$—O—$(CH_2)_2$—$SO_2$—Y,
—NH—CO—CHW—$CH_2$—W, or
—NH—CO—C(W)=$CH_2$ Wherein Y being selected from the list —CH=$CH_2$ or —$CH_2$—$CH_2$—U, and U and W are a group removable under alkaline conditions.

According to embodiments, U and W in the reactive cross-linking (tanning) agent according to the invention (see compounds according to formula [1]) are independently from each other selected from —Cl, —Br, —F, —$OSO_3H$, —$SO_3H$, —OCO—$CH_3$, —$OPO_3H_2$, —OCO—$C_6H_5$, —$OSO_2$-$C_1$-$C_4$alkyl or $OSO_2N(C_1$-$C_4$alkyl)$_2$, preferably U and W are independently from each other selected from —Cl, —$OSO_3H$, —$SO_3H$, —OCO—$CH_3$, —OCO—$C_6H_5$ or —$OPO_3H_2$, more preferably U and W are independently from each other selected from —Cl or —$OSO_3H$, most preferably U and W are selected from —$OSO_3H$.

According to embodiments, $K_1$, $K_2$, $K_3$ and $K_4$ in the reactive cross-linking (tanning) agent according to the invention (see compounds according to formula [1]) are each independently from each other selected from H, —$SO_2$—CH=$CH_2$ or —$SO_2$—$CH_2$—$CH_2$—U and wherein U is a group removable under alkaline conditions.

According to embodiments, the protein-based substrates are preferably selected from collagen containing fibrous material (both natural and synthetic), more preferably selected from (animal) hides or skins.

According to embodiments the reactive cross-linking (tanning) agent according to the invention (compounds according to formula [I]) is preferably selected from one of the following examples 1-15 in Tables 1-3 below:

TABLE 1

| | Example | | | | | |
|---|---|---|---|---|---|---|
| | 1 | 2 | 3 | 4 | 5 | 6 |
| L1 | H | H | H | H | H | H |
| L2 | H | H | H | H | H | H |
| L3 | H | H | H | H | H | H |
| L4 | H | H | H | H | H | H |
| L5 | H | H | H | H | H | H |
| L6 | H | H | H | O—CH$_3$ | H | H |
| L7 | H | H | H | H | O—CH$_3$ | CH$_3$ |
| L8 | H | H | H | H | O—CH$_3$ | O—CH$_3$ |
| K1 | SO$_2$—CH$_2$—CH$_2$—OSO$_3$H | SO$_2$—CH$_2$—CH$_2$—OSO$_3$H | SO$_2$—CH=CH$_2$ | SO$_2$—CH$_2$—CH$_2$—OSO$_3$H | SO$_2$—CH$_2$—CH$_2$—OSO$_3$H | SO$_2$—CH$_2$—CH$_2$—OSO$_3$H |
| K2 | H | H | H | H | H | H |
| K3 | SO$_2$—CH$_2$—CH$_2$—OSO$_3$H | H | SO$_2$—CH=CH$_2$ | H | SO$_2$—CH$_2$—CH$_2$—OSO$_3$H | SO$_2$—CH$_2$—CH$_2$—OSO$_3$H |
| K4 | H | SO$_2$—CH$_2$—CH$_2$—OSO$_3$H | H | SO$_2$—CH$_2$—CH$_2$—OSO$_3$H | H | H |
| X | Cl | Cl | F | Cl | Cl | Cl |

TABLE 2

| | Example | | | | |
|---|---|---|---|---|---|
| | 7 | 8 | 9 | 10 | 11 |
| L1 | H | H | H | H | H |
| L2 | H | H | H | H | H |
| L3 | H | H | H | H | H |
| L4 | H | H | H | H | H |
| L5 | H | CH$_2$CH$_3$ | H | H | H |
| L6 | OH | H | H | H | OH |
| L7 | SO$_3$H | H | H | H | SO$_3$H |
| L8 | H | H | H | H | H |
| K1 | SO$_2$—CH$_2$—CH$_2$—OSO$_3$H | SO$_2$—CH$_2$—CH$_2$—OSO$_3$H | H | H | H |
| K2 | H | H | SO$_2$—CH$_2$—CH$_2$—OSO$_3$H | SO$_2$—CH=CH$_2$ | SO$_2$—CH=CH$_2$ |
| K3 | H | H | H | H | H |
| K4 | SO$_2$—CH$_2$—CH$_2$—OSO$_3$H | SO$_2$—CH$_2$—CH$_2$—OSO$_3$H | SO$_2$—CH$_2$—CH$_2$—OSO$_3$H | SO$_2$—CH=CH$_2$ | SO$_2$—CH=CH$_2$ |
| X | Cl | Cl | Cl | F | F |

TABLE 3

| | Example | | | |
|---|---|---|---|---|
| | 12 | 13 | 14 | 15 |
| L1 | H | H | H | H |
| L2 | H | H | H | H |
| L3 | H | H | H | H |
| L4 | H | H | H | H |
| L5 | H | H | H | H |
| L6 | OH | H | H | OCH$_3$ |
| L7 | SO$_3$H | H | H | H |
| L8 | H | H | H | H |
| K1 | H | SO$_2$—CH$_2$—CH$_2$—OSO$_3$H | SO$_2$—CH=CH$_2$ | SO$_2$—CH$_2$—CH$_2$—OSO$_3$H |
| K2 | SO$_2$—CH=CH$_2$ | H | H | H |
| K3 | H | SO$_2$—CH=CH$_2$ | H | H |
| K4 | SO$_2$—CH$_2$—CH$_2$—OSO$_3$H | H | SO$_2$—CH$_2$—CH$_2$—OSO$_3$H | SO$_2$—CH=CH$_2$ |
| X | F | Cl | Cl | Cl |

According to preferred embodiments the reactive cross-linking (tanning) agent according to the invention is selected from compounds according to formula [2], [3], [4], [5] or [6]:

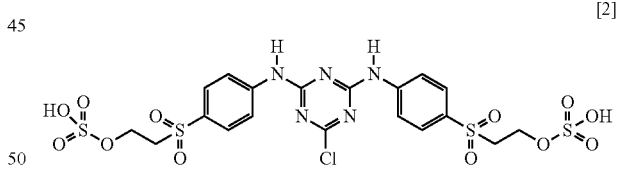

[2]

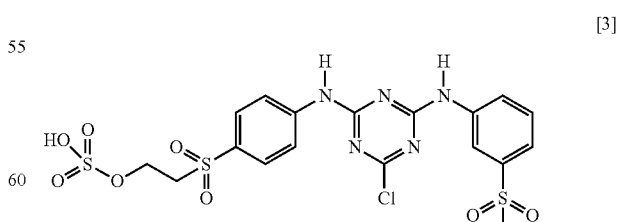

[3]

-continued

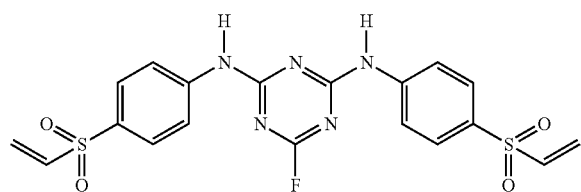
[4]

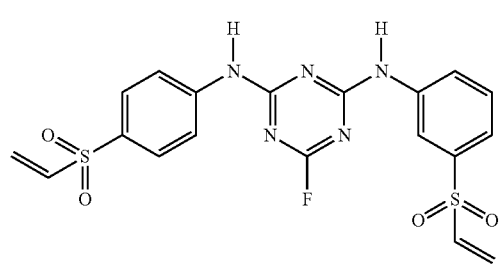
[5]

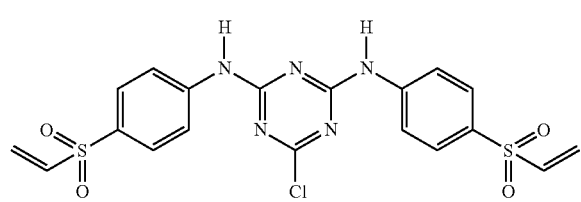
[6]

According to alternative embodiments the reactive cross-linking (tanning) agent according to the invention is selected from compounds according to formula [7], [8], [9] or [10]:

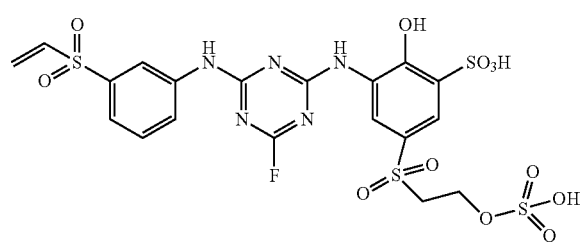
[7]

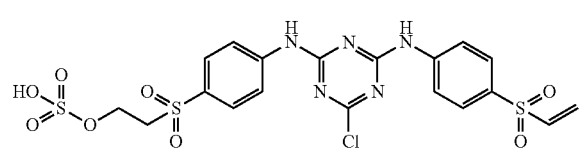
[8]

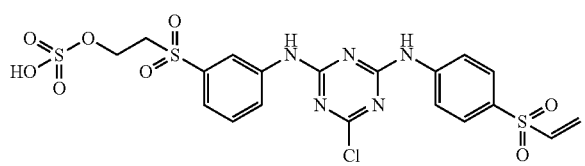
[9]

-continued

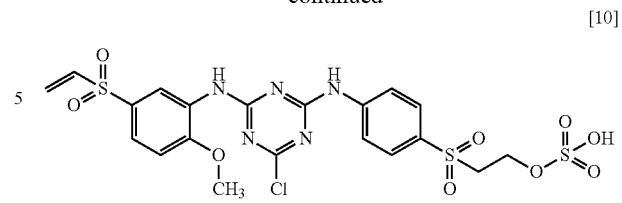
[10]

According to embodiments, the reactive cross-linking (tanning) agent according to the invention forms at least a bivalent covalent linkage between the amine (such as but not limited to —$NH_2$) and possibly —OH groups on the protein-containing substrate thereby providing a tanning effect.

According to embodiments, the reactive cross-linking (tanning) agent according to the invention will generate a metal-free substrate ("metal-free leather") after cross-linking (tanning).

According to embodiments, the reactive cross-linking (tanning) agent according to the invention can generate effects known in the leather industry as pre-tanning, main tanning (also known as full or complete tanning whether used alone or in combination with other known tanning agents) or retanning.

According to embodiments, the colourless reactive cross-linking (tanning) agent according to the invention will generate a cross-linking effect on protein-based substrates, more in particular this means that the cross-linking (tanning) agent according to the invention is able to generate modification of the protein by at least a bivalent crosslinking by the reactive cross-linking (tanning) agent.

According to embodiments, compared to state of the art cross-linking (tanning) agents, the cross-linking (tanning) agent according to the invention may avoid or eliminate the use of NaCl in the cross-linking (tanning) process.

According to embodiments, the use of the colourless reactive protein cross-linking (tanning) agent according to the invention allows to create a white or natural coloured substrate (leather). Typically state of the art tanning agents for leather impart some sort of colour (e.g. chrome gives a blue/green hue, glutaraldehyde a cream/yellow colour, vegetable tanning typically gives a range of brown colours, etc).

According to embodiments, the use of the reactive protein cross-linking (tanning) agent according to the invention typically gives a hydrothermal stability (the wet shrinkage temperature) in the range of 70° C. to 85° C., preferably 75° C. to 82° C., most preferably 75° C.-80° C.

According to embodiments, the use of the reactive protein cross-linking (tanning) agent according to the invention gives a hydrothermal stability (the wet shrinkage temperature) of at least 70° C., preferably at least 75° C.

According to embodiments, the use of the reactive protein cross-linking (tanning) agent according to the invention offers enhanced properties to the treated substrates such as long-term cross-linking (tanning) stability.

According to embodiments, the use of the reactive protein cross-linking (tanning) agent according to the invention allows to create more brilliant colours in the (subsequent or simultaneous) dyeing process.

According to embodiments, the reactive protein cross-linking (tanning) agent according to the invention may be used in combination with state of the art protein cross-linking (tanning) agents.

According to embodiments, the colourless protein reactive cross-linking (tanning) agent according to the invention may be used in combination with state of the art dyes. Said state of the art dyes may be used simultaneously with the reactive cross-linking (tanning) agent according to the invention meaning that cross-linking (tanning) and dyeing occur in 1 step. Alternatively said state of the art dyes may be used in a separate step after the cross-linking (tanning) step meaning that cross-linking (tanning) and dyeing occur in 2 distinguishing steps.

According to embodiments, the use of the reactive protein cross-linking (tanning) agent according to the invention in combination with state of the art dyes allows to create a leather with a pastel or medium depth of shade.

According to embodiments, the colourless protein reactive cross-linking (tanning) agent according to the invention may be used in combination with state of the art reactive dyes.

According to preferred embodiments, the state of the art reactive dyes which may be used in combination with the colourless reactive cross-linking (tanning) agent according to the invention may be selected from mono, bi, tri and/or poly functional reactive dyes.

According to embodiments, said reactive dye may be selected from bi, tri and/or poly functional reactive dyes having cross-linking properties with the protein-based substrates and hence may act as an additional coloured tanning agent in combination with the colourless reactive cross-linking (tanning) agent according to the invention. Said reactive dye may be selected from compounds according to formula [20] or [21]

$$A_1 \text{—} (Z_1)_{2\text{-}3}, \text{ and} \quad [20]$$

[21]

(structure showing: $Z_2\text{—}A_2\text{—}N(Q_1)\text{—}$ triazine with $G_1$ $\text{—}N(Q_2)\text{—}B\text{—}N(Q_3)\text{—}$ triazine with $G_2$ $\text{—}N(Q_4)\text{—}A_3\text{—}Z_3$, bracketed subscript $b$)

wherein $A_1$, $A_2$ and $A_3$ are each independently of the others the radical of a monoazo, polyazo, metal-complexed azo, anthraquinone, phthalo-cyanine, formazan or dioxazine chromophore having at least one sulfo group, B is an organic bridge member, $Q_1$, $Q_2$, $Q_3$ and $Q_4$ are each independently of the others hydrogen or unsubstituted or substituted $C_1$-$C_4$alkyl, and $G_1$ and $G_2$ are halogen, 3-carboxypyridin-1-yl or 3-carbamoylpyridin-1-yl, $(Z_1)_{2\text{-}3}$ is 2 to 3 identical or different protein reactive radicals, and $Z_2$ and $Z_3$ are each independently of the other identical or different protein reactive radicals, and b is the number 0 or 1.

According to preferred embodiments, $A_1$, $A_2$ and $A_3$ are each independently of the others selected from a monoazo or polyazo chromophore in the reactive dyes according to formula [20] or [21].

According to preferred embodiments, $A_1$, $A_2$ and $A_3$ in the reactive dyes according to formula [20] or [21] are each independently of the others selected from a radical of the formula:

[25]

(phenyl-$(R_4)_{0\text{-}3}$—N=N—naphthyl with $(R_5)_{0\text{-}2}$ and $(SO_3H)_{1\text{-}3}$, bracketed with $q$ bonds)

wherein $(R_4)_{0\text{-}3}$ denotes from 0 to 3 identical or different substituents from the group $C_1$-$C_4$alkyl, $C_1$-$C_4$alkoxy, $C_2$-$C_4$alkanoylamino, ureido, sulfamoyl, carbamoyl, sulfomethyl, halogen, amino, hydroxy, carboxy and sulfo, $(R_5)_{0\text{-}2}$ denotes from 0 to 2 identical or different substituents from the group hydroxy, amino, N-mono-$C_1$-$C_4$alkylamino, N,N-di-$C_1$-$C_4$alkylamino, $C_2$-$C_4$alkanoylamino and benzoylamino, and q in formula (25) is the number 2 or 3, that is q depicts 2 or 3 bonds attached to the chromophore;

[26]

(naphthyl with $(SO_3H)_{1\text{-}3}$—N=N—naphthyl with $(R_5)_{0\text{-}2}$ and $(SO_3H)_{1\text{-}3}$, bracketed with $q$ bonds)

wherein $(R_5)_{0\text{-}2}$ is as defined above, and q in formula (26) is the number 2 or 3, that is q depicts 2 or 3 bonds attached to the chromophore;

[27]

(phenyl with $(R_6)_{0\text{-}3}$—N=N—pyrazole with OH, NH$_2$ and CH$_3$,COOH—N-phenyl with $(R_7)_{0\text{-}3}$, bracketed with $q$ bonds)

wherein $(R_6)_{0\text{-}3}$ and $(R_7)_{0\text{-}3}$ independently of the other denotes from 0 to 3 identical or different substituents from the group $C_1$-$C_4$alkyl, $C_1$-$C_4$alkoxy, halogen, carboxy and sulfo, and q in formula (27) is the number 2 or 3, that is q depicts 2 or 3 bonds attached to the chromophore;

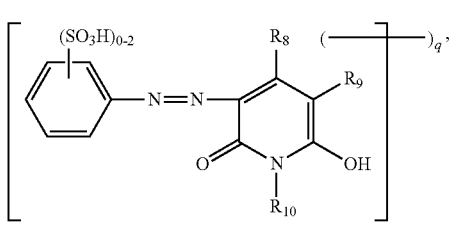

wherein
- $R_8$ and $R_{10}$ are each independently of the other hydrogen, $C_1$-$C_4$alkyl or phenyl,
- $R_9$ hydrogen, cyano, carbamoyl or sulfomethyl, and
- q in formula (28) is the number 2 or 3, that is q depicts 2 or 3 bonds attached to the chromophore;

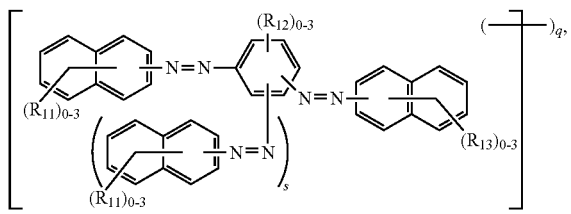

wherein
- $(R_{11})_{0-3}$ is as defined for $(R_4)_{0-3}$,
- $(R_{12})_{0-3}$ denotes from 0 to 3 identical or different substituents from the group $C_1$-$C_4$alkyl, $C_1$-$C_4$alkoxy, halogen, amino, carboxy and sulfo,
- $(R_{13})_{0-3}$ is as defined for $(R_4)_{0-3}$, or $R_{13}$ is a radical —N=N—Ph, wherein Ph is phenyl that is unsubstituted or substituted by $C_1$-$C_4$alkyl, $C_1$-$C_4$alkoxy, halogen, carboxy or sulfo,
- s is the number 0 or 1, and
- q in formula (29) is the number 2 or 3, that is q depicts 2 or 3 bonds attached to the chromophore;

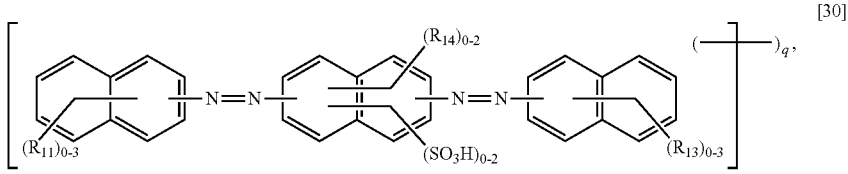

wherein
- $(R_{11})_{0-3}$ and $(R_{13})_{0-3}$ independently of the other are as defined above,
- $(R_{14})_{0-2}$ denotes from 0 to 2 identical or different substituents from the group $C_1$-$C_4$alkyl, $C_1$-$C_4$alkoxy, halogen, carboxy, sulfo, hydroxyl, amino, N-mono-$C_1$-$C_4$alkylamino, N,N-di-$C_1$-$C_4$alkylamino, $C_2$-$C_4$alkanoylamino and benzoylamino, and
- q in formula (30) is the number 2 or 3, that is q depicts 2 or 3 bonds attached to the chromophore.

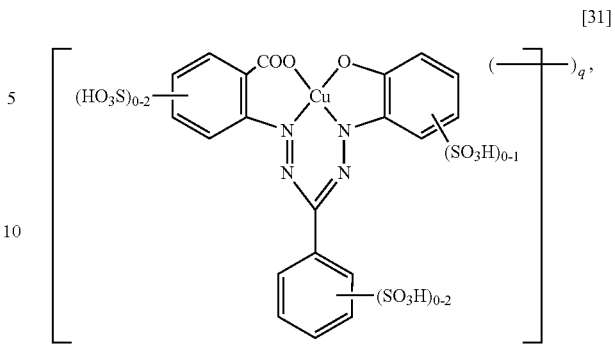

wherein
- the benzene nuclei do not contain any further substituents or are further substituted by $C_1$-$C_4$alkyl, $C_1$-$C_4$alkoxy, $C_1$-$C_4$alkylsulfonyl, halogen or by carboxy, and
- q is the number 2 or 3, that is q depicts 2 or 3 bonds attached to the chromophore;

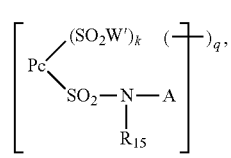

wherein
- Pc is the radical of a metal phthalocyanine, especially the radical of a copper or nickel phthalocyanine,
- W' is —OH and/or —$NR_{16}R_{16}'$ and $R_{16}$ and $R_{16}'$ are each independently of the other hydrogen or $C_1$-$C_4$alkyl that is unsubstituted or substituted by hydroxyl or by sulfo,
- $R_{15}$ is hydrogen or $C_1$-$C_4$alkyl,
- A is a phenylene radical that is unsubstituted or substituted by $C_1$-$C_4$alkyl, $C_1$-$C_4$alkoxy, halogen, carboxy or by sulfo, or is a $C_2$-$C_6$alkylene radical,
- k is from 1 to 3, and
- q is the number 2 or 3, that is q depicts 2 or 3 bonds attached to the chromophore;

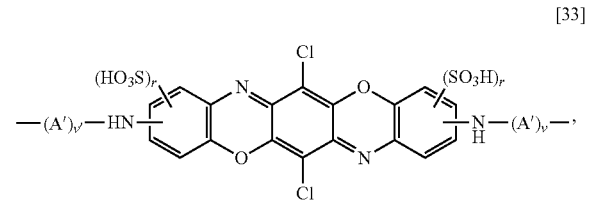

wherein
- A' is a phenylene radical that is unsubstituted or substituted by $C_1$-$C_4$alkyl, $C_1$-$C_4$alkoxy, halogen, carboxy or by sulfo, or is a $C_2$-$C_6$alkylene radical,
- r independently is the number 0, 1 or 2, preferably 0 or 1, and
- v and v' are each independently of the other the number 0 or 1.

According to preferred embodiments, the protein reactive radicals $Z_1$, $Z_2$ and $Z_3$ in the reactive dyes according to formula [20] or [21] are each independently of the others selected from a radical of the formula:

  (3a),

  (3b),

  (3c),

  (3d),

  (3e),

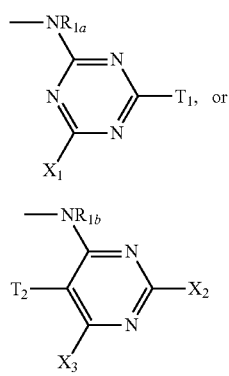

(3f)

(3g)

in which
- Hal is chlorine or bromine;
- $X_1$ is halogen, 3-carboxypyridin-1-yl or 3-carbamoylpyridin-1-yl;
- $T_1$ independently has the meaning of $X_1$, or is a substituent which is not protein reactive, or is a protein reactive radical of the formula:

  (4a)

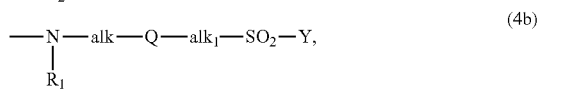  (4b)

  (4c)

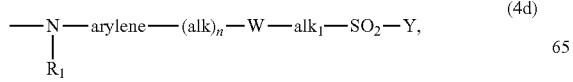  (4d)

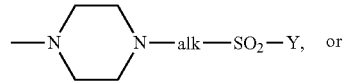  (4e)

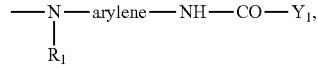  (4f)

in which
- $R_1$, $R_{1a}$ and $R_{1b}$ independently of one another are each hydrogen or $C_1$-$C_4$alkyl,
- $R_2$ is hydrogen, $C_1$-$C_4$alkyl which is unsubstituted or substituted by hydroxyl, sulfo, sulfato, carboxyl or cyano or a radical

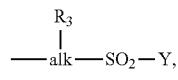

- $R_3$ is hydrogen, hydroxyl, sulfo, sulfato, carboxyl, cyano, halogen, $C_1$-$C_4$alkoxycarbonyl, $C_1$-$C_4$alkanoyloxy, carbamoyl or the group —$SO_2$—Y,
- alk and $alk_1$ independently of one another are linear or branched $C_1$-$C_6$alkylene
- arylene is a phenylene or naphthylene radical which is unsubstituted or substituted by sulfo, carboxyl, $C_1$-$C_4$alkyl, $C_1$-$C_4$alkoxy or halogen,
- Q is a radical —O— or —$NR_1$—, in which $R_1$ is as defined above,
- W is a group —$SO_2$—$NR_2$—, —$CONR_2$— or —$NR_2CO$—, in which $R_2$ is as defined above,
- Y is vinyl or a radical —$CH_2$—$CH_2$—U and U is a group which can be split off under alkaline conditions,
- $Y_1$ is a group —CH(Hal)—$CH_2$—Hal or —C(Hal)=$CH_2$ and Hal is chlorine or bromine and
- l and m independently of one another are an integer from 1 to 6 and n is the number 0 or 1;

and
- $X_2$ is halogen or $C_1$-$C_4$alkylsulfonyl;
- $X_3$ is halogen or $C_1$-$C_4$alkyl; and
- $T_2$ is hydrogen, cyano or halogen.

According to preferred embodiments, the protein reactive radicals $Z_1$, $Z_2$ and $Z_3$ in the reactive dyes according to formula [20] or [21] are each independently of the others selected from a radical of the (3a), (3b) or (3f) in which
- Y is vinyl, β-chloroethyl or β-sulfatoethyl,
- $R_2$ and $R_{1a}$ are hydrogen,
- l is the number 2 or 3,
- $X_1$ is halogen,
- $T_1$ is $C_1$-$C_4$alkoxy, $C_1$-$C_4$alkylthio, hydroxyl, amino, N-mono- or N,N-di-$C_1$-$C_4$alkylamino which are unsubstituted or substituted in the alkyl moiety by hydroxy, sulfato or sulfo, morpholino, phenylamino or N-$C_1$-$C_4$ alkyl-N-phenylamino which are unsubstituted or substituted in the phenyl ring by sulfo, carboxy, acetylamino, chlorine, methyl or methoxy and in which the alkyl is unsubstituted or substituted by hydroxy, sulfo or sulfato, or naphthylamino which is unsubstituted or substituted by 1 to 3 sulfo groups, or
- $T_1$ is a fiber reactive radical of the formula

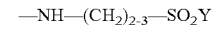  (4a'),

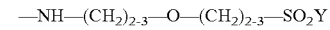  (4b'),

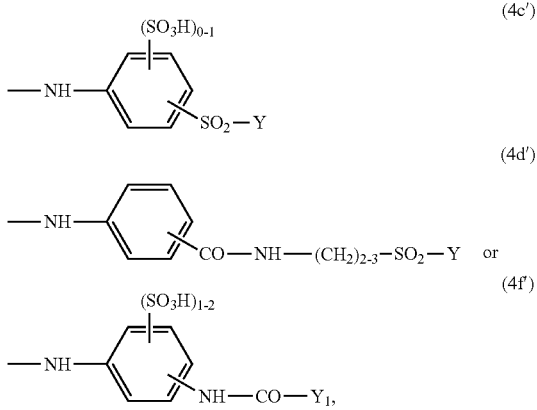

in which
Y is as defined above and
$Y_1$ is a group —CH(Br)—CH$_2$—Br or —C(Br)=CH$_2$.

According to preferred embodiments, the reactive dyes according to formula [20] or [21] or comprise an organic bridge member B which is selected from a C2-C6 alkylene radical, which may be interrupted by 1, 2 or 3 —O— members and is unsubstituted or substituted by hydroxyl, or phenylene substituted by one or two sulfo groups, and wherein G1 and G2 are preferably each independently of the other chlorine or fluorine, especially chlorine.

According to embodiments, the colourless reactive cross-linking (tanning) agent according to the invention may be used in combination with state of the art dyes selected from reactive dyes including monoazo, polyazo, metal-complexed azo, anthraquinone, phthalocyanine, formazan or dioxazine dyestuff, such as Reactive Black 5 but not limited to this given example.

According to embodiments, the reactive cross-linking (tanning) agent according to the invention can be used in combination with a state of the art dye selected from at least one acid dye comprising acidic groups, such as but not limited to SO$_3$H and COOH. An example of an acid dye is Acid Black 210.

The current invention further provides a process for cross-linking (tanning) a protein-based substrate having amine and optionally OH functionality, said process comprising treating the protein-based substrate with the colourless reactive cross-linking (tanning) agent according to the invention with a suitable amount of said colourless reactive cross-linking (tanning) agent. Typically, the protein-based substrate is placed in a liquid medium (at a suitable pH) in a suitable processing vessel such as a rotating drum at a temperature in the range 10° C. to 50° C., preferably 20° C. to 40° C., most preferably 25° C. to 30° C. and a suitable amount of colourless reactive cross-linking (tanning) agent is added to the liquid medium. Preferably the amount of cross-linking agents is in the range between 1 wt % and 40 wt %, preferably between 10 wt % and 30 wt %, and more preferably between 16 wt % and 25 wt % based on the dry weight of the protein-based substrate. The rotating drum is then run for a period of time to achieve sufficient penetration of the cross-linking agents into the protein-based substrate. After penetration, the pH of the liquid medium, and consequently the protein-based substrate is typically raised in order for the colourless cross-linking (tanning) agent to react with the protein reactive groups in the protein-based substrate to complete the cross-linking (tanning) reaction. The cross-linked substrate then typically requires rinsing/washing to remove excess reactants, salts, alkalis, alkaline buffers used during the cross-linking process.

According to embodiments, the protein-based substrate is a collagenous substrate such as pelts, skins and hides and the tanning process starts after the deliming step. Preferably the tanning is typically performed in a liquid medium in a rotating drum at a temperature in the range 10° C. to 50° C., preferably 20° C. to 40° C., most preferably 25° C. to 30° C. The pH of the liquid medium and the collagenous substrates (hides, skins, pelts, etc) is preferably in the range 4.0 to 9.0, preferably 6.0 to 7.5, most preferably 6.5 to 7.0 and the amount of colourless reactive cross-linking (tanning) agent added to the liquid medium to achieve tanning of the collagen containing substrate is preferably in the range of 0.25 wt % to 10 wt %, preferably 2.5 wt % to 7.5 wt %, most preferably 4 wt % to 6 wt % based on the limed weight of the collagenous substrates. The time required to achieve sufficient penetration of the cross-linking (tanning) agent into the fibre structure of the collagenous substrate typically ranges from 15 minutes to 720 minutes, preferably 30 minutes to 360 minutes, most preferably 60 minutes to 120 minutes. After penetration of the cross-linking (tanning) agent the pH of the liquid medium, and consequently the collagenous substrate (hide, skin or pelt), is then raised in order for the colourless cross-linking (tanning) agent to react with the collagen in the collagenous substrate (hide, skin or pelt) to complete the cross-linking (tanning) reaction. This is typically achieved through addition of products that will provide alkalinity to the system, and include not only alkalis but also alkali buffer systems. Examples include, but are not limited to, sodium and/or potassium bicarbonate, sodium and/or potassium carbonate, sodium and/or potassium hydroxide, sodium and/or potassium formate, sodium and/or potassium hydrogen phosphate, sodium borate, etc. The pH is then typically increased to a range of 7.5 to 12, preferably 8.5 to 11, most preferably 9 to 10 for a further time period and the temperature of the drum may be optionally further increased. The tanned substrate (leather) then requires rinsing/washing to remove excess reactants, salts, alkalis, alkaline buffers used during the cross-linking (tanning) process and the pH to be reduced to return the leather closer to its iso-electric point and ensure it is in a suitable pH range for subsequent process at a later time.

The current invention further provides a process for simultaneously cross-linking (tanning) and dyeing a protein-based substrate having amine and optionally OH functionality, said process comprising treating the protein-based substrate with a suitable amount of a colourless reactive cross-linking (tanning) agent according to the invention and at least one reactive dye having protein-reactive groups (such as but not limited to reactive dyes according to formula [20] and [21]). Preferably the amount of cross-linking agents is in the range between 1 wt % and 39 wt %, more preferably in the range between 5 wt % and 25 wt % and most preferably in the range between 10 wt % and 20 wt % based on the weight of the dry protein-based substrate. Preferably the amount of reactive dyes is in the range between 1 wt % and 39 wt %, more preferably in the range between 5 wt % and 25 wt % and most preferably in the range between 10 wt % and 20 wt % based on the weight of the dry protein-based substrate. Typically, the protein-based substrate is placed in a liquid medium (at a suitable pH) in a suitable processing vessel such as a rotating drum at a temperature in the range 10° C. to 50° C., preferably 20° C. to 40° C., most preferably 25° C. to 30° C. and a suitable amount of colourless reactive cross-linking (tanning) agent and a reactive dye having protein-reactive groups is added to the liquid medium. The rotating drum is then run for a period of time to achieve sufficient penetration of the cross-linking and dyes into the protein-based substrate. After penetration, the pH of the liquid medium, and consequently the protein-based substrate is typically raised in order for the colourless cross-linking (tanning) agent and dye to react with the protein reactive groups in the protein-based substrate to complete the cross-linking (tanning) reaction. The cross-linked and coloured substrate then typically requires rinsing/washing to remove excess reactants, salts, alkalis, alkaline buffers used during the cross-linking and dyeing process.

According to embodiments, the process for simultaneously cross-linking (tanning) and dyeing a protein-based substrate having amine and optionally OH functionality comprises treating the protein-based substrate with a suitable amount of a colourless reactive cross-linking (tanning) agent according to the invention and at least one mono-reactive dye having one protein-reactive groups. Preferably the amount of cross-linking agents is in the range between 1 wt % and 39 wt %, more preferably in the range between 10 wt % and 30 wt % and most preferably in the range between 16 wt % and 25 wt % based on the weight of the dry protein-based substrate. Preferably the amount of mono-reactive dye is in the range between 1 wt % and 25 wt %, more preferably in the range between 5 wt % and 20 wt % and most preferably in the range between 7.5 wt % and 15 wt % based on the weight of the dry protein-based substrate According to embodiments, the process for simultaneously cross-linking (tanning) and dyeing a protein-based substrate having amine and optionally OH functionality comprises treating the protein-based substrate with a suitable amount of a colourless reactive cross-linking (tanning) agent according to the invention and at least one bi-, tri- and/or polyreactive dye having protein-reactive groups (such as but not limited to reactive dyes according to formula [20] and [21]). Preferably the amount of cross-linking agents is in the range between 1 wt % and 39 wt %, more preferably in the range between 10 wt % and 30 wt % and most preferably in the range between 16 wt % and 25 wt % based on the weight of the dry protein-based substrate. Preferably the amount of bi-, tri- and/or polyreactive dye is in the range between 1 wt % and 39 wt %, more preferably in the range between 10 wt % and 30 wt % and most preferably in the range between 16 wt % and 25 wt % based on the weight of the dry protein-based substrate.

According to embodiments, the process having simultaneously cross-linking (tanning) and dyeing of a protein-based substrate allows to create pastel or medium shade colours (depths).

According to embodiments, the protein-based substrate is a collagenous substrate such as pelts, skins and hides and the simultaneous cross-linking (tanning) and dyeing process starts after the deliming step. Preferably the simultaneous cross-linking (tanning) and dyeing process is performed in a liquid medium in a suitable processing vessel such as a rotating drum at a temperature in the range 10° C. to 50° C., preferably 20° C. to 40° C., most preferably 25° C. to 30° C. The pH of the liquid medium and the collagenous substrates (hides, skins, pelts, etc) is preferably in the range 4.0 to 9.0, more preferably in the range 6.0 to 7.5, most preferably in the range 6.5 to 7.0 and the amount of the colourless reactive cross-linking (tanning) agent and reactive dye having protein-reactive groups is preferably such that the combined wt % ranges between 0.25 wt % to 10 wt %, preferably 2.5 wt % to 7.5 wt %, most preferably 4 wt % to 6 wt % based on the limed weight of the collagenous substrates. The time required to achieve sufficient penetration of the cross-linking (tanning) agent and a dye (such as but not limited to a bi-, tri- and/or poly-reactive dye) into the fibre structure of the collagenous substrate typically ranges from 15 minutes to 720 minutes, preferably 30 minutes to 360 minutes, most preferably 60 minutes to 120 minutes. After penetration the pH of the liquid medium, and consequently the collagenous substrate (hide, skin or pelt), is then raised in order for the colourless cross-linking (tanning) agent and dye to react with the collagen in the collagenous substrate (hide, skin or pelt) to complete the cross-linking (tanning) reaction. This is typically achieved through addition of products that will provide alkalinity to the system, and include not only alkalis but also alkali buffer systems. Examples include, but are not limited to, sodium and/or potassium bicarbonate, sodium and/or potassium carbonate, sodium and/or potassium hydroxide, sodium and/or potassium formate, sodium and/or potassium hydrogen phosphate, sodium borate, etc. The pH is then typically increased to a range of 7.5 to 12, preferably 8.5 to 11, most preferably 9 to 10 for a further time period and the temperature of the drum may be optionally further increased. The tanned and coloured substrate (leather) then requires rinsing/washing to remove excess reactants, salts, alkalis, alkaline buffers used during the cross-linking (tanning) process and the pH to be reduced to return the leather closer to its iso-electric point and ensure it is in a suitable pH range for subsequent process at a later time.

The current invention further provides a process for cross-linking (tanning) and dyeing a protein-based substrate having amine and optionally OH functionality, said process comprising first treating the protein-based substrate with the colourless reactive cross-linking (tanning) agent according to the invention and then treating the protein-based substrate with a dye (or conversely the other way around). Typically, the protein-based substrate is placed in a liquid medium (at a suitable pH) in a suitable processing vessel (such as a rotating drum) at a temperature in the range 10° C. to 50° C., preferably 20° C. to 40° C., most preferably 25° C. to 30° C. and in a first step a suitable amount of colourless reactive cross-linking (tanning) agent is added to the processing vessel (drum). In a next step, a suitable amount of dye is added to the liquid medium to achieve dyeing of the cross-linked (tanned) substrate (or conversely the other way around). The vessel (rotating drum) is then run for a period of time to achieve sufficient penetration of the cross-linking agent and dye into the protein-based substrate. After penetration, the pH of the liquid medium, and consequently the protein-based is typically raised in order for the colourless cross-linking (tanning) agent to react with the protein reactive groups in the protein-based substrate to complete the cross-linking (tanning) reaction. The cross-linked and coloured substrate then typically requires rinsing/washing to remove excess reactants, salts, alkalis, alkaline buffers used during the cross-linking and dyeing process.

According to embodiments, the process for cross-linking (tanning) and dyeing a protein-based substrate having amine and optionally OH functionality comprises first treating the protein-based substrate with the colourless reactive cross-linking (tanning) agent according to the invention and then treating the protein-based substrate with a dye (or conversely the other way around) wherein the amount of the colourless reactive cross-linking agent and dye is such that the combined wt % ranges between 1 wt % to 40 wt %, preferably 10 wt % to 30 wt %, most preferably 16 wt % to 25 wt % based on the dry weight of the protein-based substrates.

The invention further discloses a cross-linked (tanned) protein-based substrate, preferably a cross-linked (tanned) collagenous substrate (hides, skins, pelts), synthetic proteins, silk, etc. to achieve a cross-linked (tanned) and/or coloured leather, and/or silk substrate thereby using the reactive cross-linking (tanning) agent of the present invention according to formula [1].

The invention further discloses a cross-linked (tanned) and coloured (dyed) protein-based substrate, preferably a cross-linked (tanned) and coloured (dyed) collagenous substrate (hides, skins, pelts), synthetic proteins, silk, etc to achieve a tanned and coloured leather, and/or silk substrate thereby using the reactive cross-linking (tanning) agent of the present invention according to formula [1] in combination with a (reactive) dye such as but not limited to mono, bi, tri and/or poly functional reactive dyes having protein reactive groups (such as but not limited to reactive dyes according formula [20] and [21]). Preferably the cross-linking (tanning) and dyeing of the protein-based substrate are performed simultaneously, alternatively the step of cross-linking (tanning) is performed first and then the step of dyeing is performed (or conversely the other way around).

FIGURES

Figure 1:
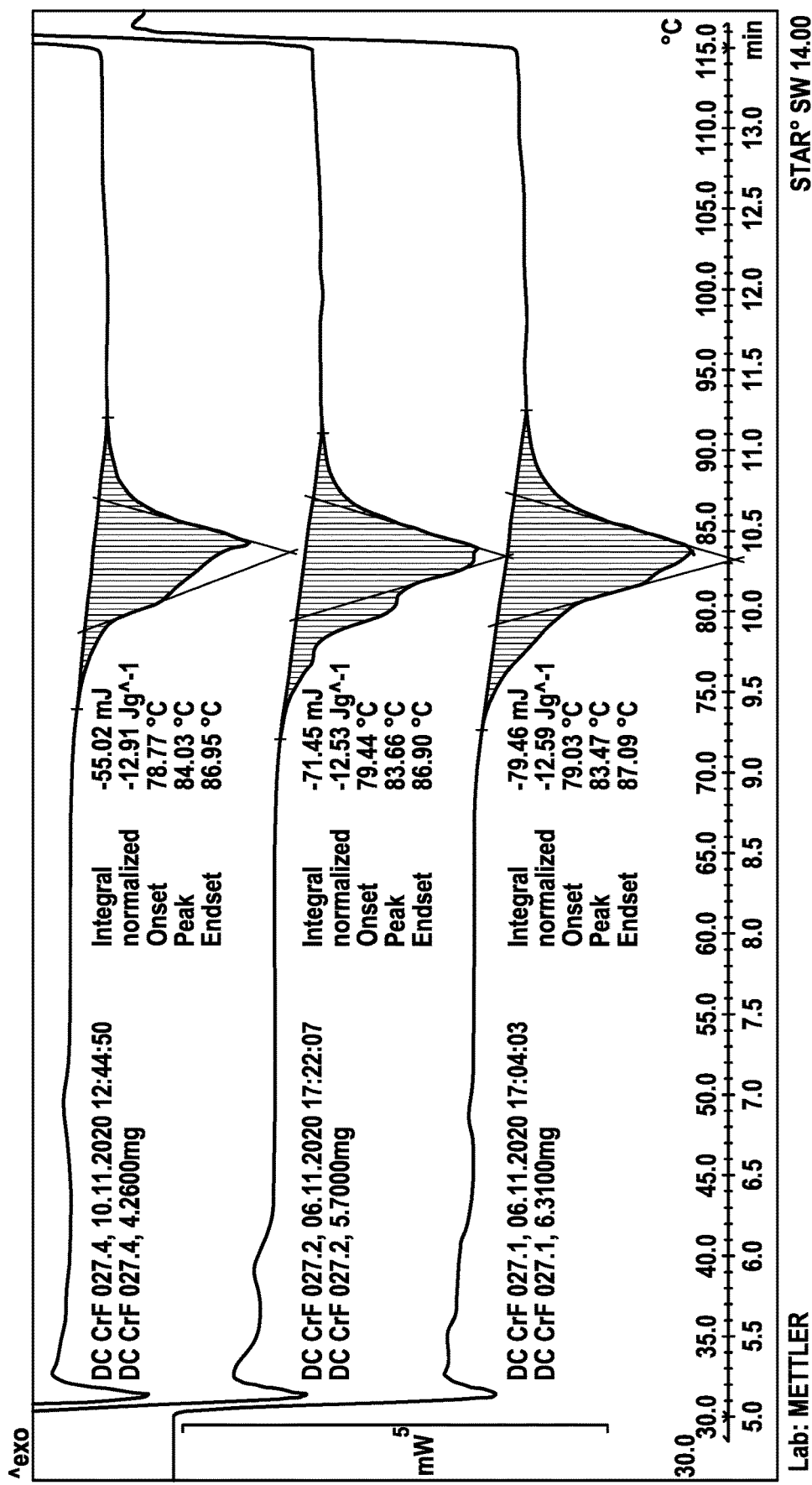
FIG. 1 shows Differential Scanning calorimetry (DSC) graphs (3 repeats) illustrating the hydrothermal stability for specific example A according to the invention (the 'Onset' temperature is the value taken as the hydrothermal stability).

The invention is illustrated with the following examples.

EXAMPLES

Methods:
Measurement Hydrothermal Stability

The hydrothermal stability of the tanned leather is tested by a hydrothermal Shrinkage tester according to method ISO 3380:2015 and tested to irreversible shrinkage. Alternatively, Differential Scanning calorimetry (DSC) is used, typically utilising heating rates of 5-10° C. per minute in sealed aluminium pans detecting the endothermic peak of the denaturation point and assessing for the 'onset' temperature.

Measurement Colour Fastness

Colour Fastness to Water and Perspiration are tested in accordance with SLF 412 (IUF 421) and SLF 426 (IUF 426), respectively.

The following generic examples 1-3 are illustrating processing conditions for the cross-linking (tanning) process with and without simultaneous dyeing of natural collagenous substrates (skins, hides, pelts, etc) thereby using the cross-linking agent according to formula [1]. The wt % of cross-linking agent (and dye) and other processing agents mentioned in below examples is based upon the limed weight of the collagenous substrates (skins, hides, pelts, etc.) In the case of leather processing, the process of tanning typically starts after the deliming process which is the last step in the so called 'Beamhouse Processing' in which stages all of the hair, fat and non-collagenous matter is removed from the hide or skin either chemically or mechanically. The deliming, bating and degreasing processes will be completed in the usual manner and employing the usual chemistries and equipment. In this invention, it is preferred to put particular emphasis on removal of calcium ions and avoidance of ammonium based salts. The below examples are illustrative and the invention is not limited hereto.

Generic Example 1: Tanning Process for
Collagenous Substrates (Hides, Skins, Pelts, etc)
with Sole Use of the Colourless Reactive Tanning
Agent According to the Invention (a) Typical equipment employed is a rotating drum, as is well known to the leather industry. It should remain rotating throughout the following process, with the exception of required powder additions, necessary technical checks (e.g. pH, temperature, etc) and for draining processes.

(b) The tanning process using the colourless reactive cross-linking (tanning) agent according to formula [1] is completed in a liquid medium having 1% to 150%, preferably 10% to 75%, most preferably 20% to 40% by weight of water based on the limed weight of the collagenous substrates. The temperature of the liquid medium is in the range 10° C. to 50° C., preferably 20° C. to 40° C., most preferably 25° C. to 30° C.

(c) The pH range of the liquor and the collagenous substrates (hides, skins, pelts, etc) is 4.0 to 9.0, preferably 6.0 to 7.5, most preferably 6.5 to 7.0. This can be measured through use of suitable pH indicator solutions (such as Bromothymol Blue) to check the collagenous substrates (hides, skins, pelts, etc) and a pH meter for the liquor.

(d) To the drum is then typically added a salt to help suppress the ionic charges on the collagen of collagenous substrates (hides, skins, pelts, etc). Examples include, but are not limited to sodium chloride, sodium sulfate, sodium formate and sodium succinate. Typical additions of the salts are in the range from 0.1 wt % to 10 wt %, preferably 1 wt % to 7.5 wt %, most preferably 2 wt % to 4 wt % (based on the limed weight of the collagenous substrates). This is typically run for a period of 1 to 120 minutes, preferably 10 minutes to 60 minutes, most preferably 15 to 30 minutes. Alternatively, said salts can be added together with the cross-linking (tanning) agent according to formula [1] or alternatively after addition of said cross-linking agent.

(e) To the drum is added a suitable amount of cross-linking (tanning) agent according to formula [1] ranging from 1 wt % to 10 wt %, preferably 2.5 wt % to 7.5 wt %, most preferably 4 wt % to 6 wt % based on the limed weight of the collagenous substrates. At this stage the intention is to gain penetration of the cross-linking (tanning) agent according to formula [1] into the fibre structure of the collagenous substrate and the time for this stage of processing may range from 15 minutes to 720 minutes, preferably 30 minutes to 360 minutes, most preferably 60 minutes to 120 minutes.

(f) The pH of the liquor, and consequently the collagenous substrate (hide, skin or pelt), is then raised in order for the colourless cross-linking (tanning) agent according to formula [1] to react with the collagen in the collagenous substrate (hide, skin or pelt) to complete the cross-linking (tanning) reaction. This is typically achieved through addition of products that will provide alkalinity to the system, and include not only alkalis but also alkali buffer systems. Examples include, but are not limited to, sodium and/or potassium bicarbonate, sodium and/or potassium carbonate, sodium and/or potassium hydroxide, sodium and/or potassium formate, sodium and/or potassium hydrogen phosphate, sodium borate, etc. The pH is then typically increased to a range of 7.5 to 12, preferably 8.5 to 11, most preferably 9 to 10. The rate at which this pH rise can be controlled through varying the additions of the alkali and/or alkaline buffer and the time for which the alkali and/or alkaline buffer is run. The range of time can be 15 minutes to 480 minutes, preferably 30 minutes to 240 minutes, most preferably 60 minutes to 120 minutes.

(g) Once the pH has reached the necessary range, the pH is typically held at such level for a further time period of 60 minutes to 1200 minutes, preferably 180 minutes to 900 minutes, most preferably 360 minutes to 600 minutes.

(h) The temperature of the drum may be increased during stages (f) and (g) above by 2° C. to 25° C., preferably 4° C. to 18° C., most preferably 6° C. to 15° C., to yield a final drum temperature in the range 25° C. to 50° C., preferably 30° C. to 45° C., most preferably 33° C. to 38° C. (if required).

(i) The drum is then drained. The time is dependent upon the size of the load and the drum configuration.

(j) The tanned substrate (leather) then requires rinsing/washing to remove excess reactants, salts, alkalis, alkaline buffers used in the preceding steps of the process and for the pH to be reduced to return the leather closer to its iso-electric point and ensure it is in a suitable pH range for subsequent process at a later time. This can be achieved in either a single step or multiple repeated steps (which is preferred). The temperature of the rinsing/washing liquor is typically between 15° C. to 55° C., preferably 20° C. to 45° C., most preferably 25° C. to 35° C. The total amount of rinsing/washing liquor is typically in the range between 100% to 750%, preferably 150% to 500%, most preferably 200% to 400% by weight of rinsing/washing liquor (based on the weight of the treated substrates). The ultimate pH of the treated substrates (leather) is typically reduced to the range of pH 3.5 to pH 8.0, preferably 4.0 to pH 6.5, most preferably pH 4.5 to pH 5.5. This can be achieved with a range of acids, acidic buffers or acidic salts, such as, but not limited to, formic acid, citric acid, acetic acid, glycolic acid, etc. The time to complete the rinsing/washing and pH reduction in totality typically ranges between 10 minutes to 300 minutes, preferably 45 minutes to 200 minutes, most preferably 75 minutes to 120 minutes. A biocide may also be added into the final washing bath as a preservative treatment for the treated substrate (tanned leather), as is well known to those skilled in the art of leather manufacture.

Generic Example 2: Simultaneous Tanning and Dyeing Process for Collagenous Substrates (Hides, Skins, Pelts, etc) With Combined Use of the Colourless Reactive Tanning Agent According to the Invention With at Least One Bi-, Tri- or Poly-Reactive Dye The same processing steps according to generic example 1 are applied here except for step e) wherein beside the reactive tanning agent according to the invention, at least one bi-, tri- or poly-reactive dye is added to the drum such that the combined wt % ranges between 1 wt % to 10 wt %, preferably 2.5 wt % to 7.5 wt %, most preferably 4 wt % to 6 wt % based on the limed weight of the collagenous substrates. The reactive tanning agent and dye may be added simultaneously or one after the other (in the same step). At this stage the intention is to gain penetration of both the cross-linking (tanning) agent according to formula [1] and the reactive dye into the fibre structure of the collagenous substrate and the time for this stage of processing may range from 15 minutes to 720 minutes, preferably 30 minutes to 360 minutes, most preferably 60 minutes to 120 minutes.

Generic Example 3: Tanning and Dyeing Process for Collagenous Substrates (Hides, Skins, Pelts, etc) With Combined Use of the Colourless Reactive Tanning Agent According to the Invention With at Least One Mono-Reactive Dye and/or Anionic Dye (e.g. Acid, Direct, Sulfur, etc)

The same processing steps according to generic example 1 are applied here except for step e) wherein a suitable amount of cross-linking (tanning) agent according to formula [1] ranging from 0.1 wt % to 10 wt %, preferably 2.5 wt % to 7.5 wt %, most preferably 4 wt % to 6 wt % based on the limed weight of the collagenous substrates is added and in addition to the tanning agent at least one mono-reactive dye and/or typical anionic dye (e.g. acid, direct, sulfur, etc) is added to the drum in an amount in a range of 0.1 wt % to 10 wt %, preferably 0.5 wt % to 7.5 wt %, most preferably 1 wt % to 5 wt % based on the limed weight of the collagenous substrate, either before, with or after the addition of the colourless cross-linking (tanning) agent according to formula [1]. At this stage (step e)) it is the intention to gain penetration of both the cross-linking (tanning) agent according to formula [1] and the reactive dye into the fibre structure of the collagenous substrate and the time for this stage of processing may range from 15 minutes to 720 minutes, preferably 30 minutes to 360 minutes, most preferably 60 minutes to 120 minutes.

To any of the generic examples above, and if desired, other non-mineral based tanning agents that are typically anionic in nature may be applied before, with or after the reactive tanning molecules according to formula [1], providing what is known to those skilled in the art of leather making as pretanning, combination tanning or retanning. Examples include, but are not limited to, synthetic, semi-synthetic and natural tanning agents based upon for example sulphones, phenols, napthols, aldehydes, aldehydic compounds, aldehyde derivatives, acrylate based polymers, sulfonyl chlorides, urethane based polymers, melamine, dicyandiamide, lignosulfonates, styrene maleic compounds, carbamoyl sulfonates, vegetable extracts, etc.

In addition, these cross-linked (tanned) and optionally dyed collagenous substrates (leathers) formed from the above examples can be further processed with chemistries and processes that are well known to those in the art of making leather commonly known as 'retan, dye and fatliquoring'. Furthermore, other chemical auxiliaries can be applied to confer characteristics to the leather that generate for example water resistance, oil and stain repellence, flame retardance, etc properties.

The following specific examples A-G are illustrating a specific cross-linking (tanning) process (with and without simultaneous dyeing) on a specific collagenous substrate thereby using the cross-linking agent according to formula [2]. The following comparative example 1 is illustrating a cross-linking process disclosed in Application Example 1 in in WO 2010/130311 thereby using the composition 2 disclosed in WO 2010/130311, said composition 2 comprises a tanning agent (A) described in Example 1 in WO 2010/130311 and corresponding to the following formula:

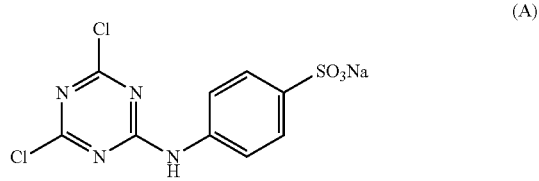

(A)

The wt % of cross-linking agent (and dye) mentioned in below examples are again based upon the limed weight of the collagenous substrates used and the processes described below also here start after the deliming process (see above).

Specific Example A: Tanning Process on UK Source Cow Hide With Sole Use of the Colourless Reactive Tanning Agent According to Formula (2)

(a) A rotating drum is used which remains rotating throughout the following process, with the exception of required powder additions, necessary technical checks (e.g. pH, temperature, etc) and for draining processes.
(b) To the drum and the cow hides was added 30 wt % of water based on the limed weight of the cow hide at 30+/−1° C.
(c) The pH range of the liquor and the hides is adjusted to 6.8+/−0.2. This is through using Bromothymol Blue indicator (a green colour should be observed) to check the cross-sectional pH of the hides and a calibrated pH meter to measure the pH of the aqueous liquor.
(d) To the drum is added 2.5 wt % of anhydrous sodium sulphate based on the limed weight of the cow hide. This is run for a period of 15 minutes.
(e) To the drum is then added 5 wt % of colourless reactive tanning agent according to formula [2] based on the limed weight of the cow hide for a period of 120 minutes.
(f) A total of 2 wt % Sodium Bicarbonate and 1.3 wt % Sodium Carbonate based on the limed weight of the cow hide is then added in four equal additions every 30 minutes to achieve a pH of 9.3 as measured by a calibrated pH meter.
(g) The drum continues to run for a period of 480 minutes, whilst periodically checking the pH of the liquor to ensure it does not fall below pH 9.2. During this time the drum naturally increases in temperature due to internal friction and increases from 30° C. to 36° C.
(h) The drum is then drained for 10 minutes.
(i) The leather is then washed with 100 wt % water at 30° C. and 1 wt % Formic acid based on the limed weight of the cow hide for a period of 30 minutes.
(j) The drum is then drained for 10 minutes.
(k) The leather is then washed with 100 wt % water at 30° C. and 1 wt % Formic acid based on the limed weight of the cow hide for a period of 30 minutes.
(l) The drum is then drained for 10 minutes.
(m) The leather is then washed with 100 wt % water at 20° C. and 0.25 wt % Formic acid based on the limed weight of the cow hide and 0.15 wt % commercially available leather biocide (Preventol WB) based on the limed weight of the cow hide for a period of 60 minutes. The pH of the liquor is checked to ensure it is 4.8+/−0.2. The cross-section of the leather is checked with Bromocresol Green indicator solution and should be a green-blue colour.
(n) The leather is then removed and aged ('horsed up') for a period of 24 hours prior to further standard leather processing.

FIG. 1 shows Differential Scanning calorimetry (DSC) graphs (3 repeats) illustrating the hydrothermal stability for specific example A according to the invention (the 'Onset' temperature is the value taken as the hydrothermal stability).

Specific Example B: Tanning and Dyeing Process on Ethiopian Hairsheep Skins With Combined Use of Colourless Reactive Tanning Agent According to Formula (2) and a Reactive Dye (a) A rotating drum is used which remains rotating throughout the following process, with the exception of required powder additions, necessary technical checks (e.g. pH, temperature, etc) and for draining processes.
(b) To the drum and the skins inside was added 40 wt % of water based on the limed weight of the skins at 27+/−1° C.
(c) The pH range of the liquor and the skins is adjusted to 6.6+/−0.2. This was measured through use of Bromocresol Purple indicator (a purple colour should be observed) to check the cross-section pH of the skins and a calibrated pH meter for the aqueous liquor.
(d) To the drum is added 2.0 wt % of anhydrous sodium sulphate based on the limed weight of the skins. This is run for a period of 15 minutes.
(e) To the drum is then added 3 wt % of colourless reactive tanning agent according to formula (2) and 2.5 wt % of reactive dye based on the limed weight of the skins over a period of 90 minutes.
(f) A penetration check is made to ensure that the dye has adequately penetrated the cross-section of the skin.
(g) A total of 1.5 wt % Sodium Bicarbonate, 1 wt % Sodium Formate and 1.5 wt % Potassium Carbonate (based on the limed weight of the skins) is added in five equal additions every 20 minutes to achieve a pH of 9.4 as measured by a calibrated pH meter.
(h) The drum continues to run for a period of 420 minutes, whilst periodically checking the pH of the liquor to ensure it does not fall below pH 9.2. During this time the drum is programmed to increase in temperature at a gradient of 1.5° C. every 60 minutes to give a final drum temperature of 37.5° C.
(i) The drum is then drained for 10 minutes.
(j) The leather is then washed with 125 wt % water based on the limed weight of the skins at 35° C. and 1.1 wt % Formic acid based on the limed weight of the skins for a period of 20 minutes.
(k) The drum is then drained for 10 minutes.
(l) The leather is then washed with 125 wt % water based on the limed weight of the skins at 25° C. and 0.8 wt % Formic acid based on the limed weight of the skins for a period of 30 minutes.

(m) The drum is then drained for 10 minutes.

(n) The leather is then washed with 80 wt % water at 20° C. and 0.3 wt % Formic acid and 0.15 wt % commercially available leather biocide (Preventol WB) based on the limed weight of the skins for a period of 90 minutes. The pH of the liquor is checked to ensure it is 4.8+/−0.2.

(o) The leather is then removed and aged ('horsed up') for a period of 18 hours prior to further standard leather processing.

Colour fastness for Specific Example B was Greyscale Rating 5 to Water Contact and Greyscale Rating 4.5 to Perspiration Contact (both assessed to the cotton zone of the multifibre strip) on both the Grain and Fleshside.

Figure 2:
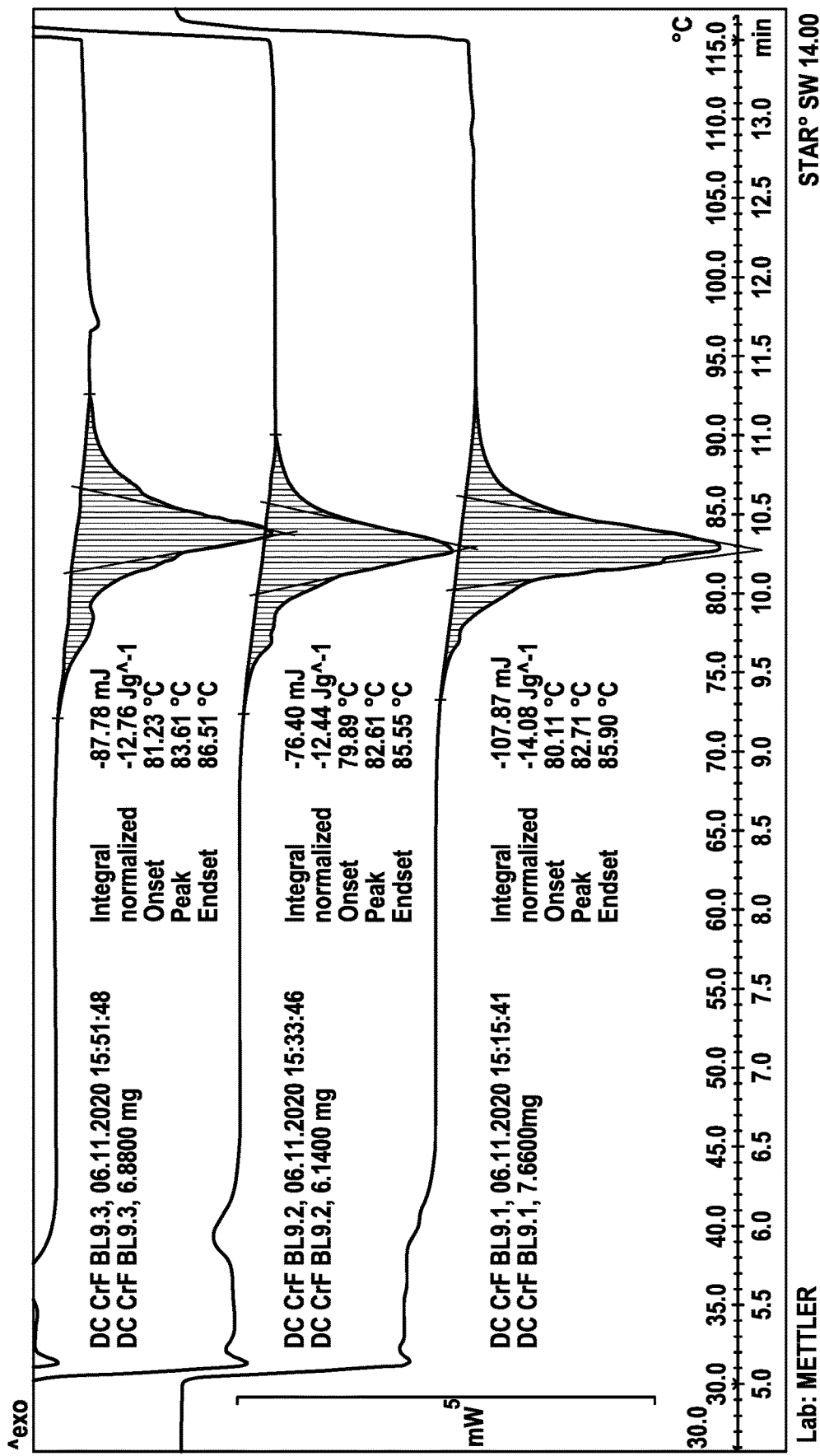
FIG. 2 shows Differential Scanning calorimetry (DSC) graphs (3 repeats) illustrating the hydrothermal stability for specific example B according to the invention (the 'Onset' temperature is the value taken as the hydrothermal stability).

FIG. 2 shows Differential Scanning Calorimetry (DSC) graphs (3 repeats) illustrating the hydrothermal stability for specific example B according to the invention (the 'Onset' temperature is the value taken as the hydrothermal stability).

Specific Example C: Tanning and Dyeing Process on Indian Goatskin With Combined Use of Colourless Reactive Tanning Agent According to Formula (2) and an Anionic Dye (a) A rotating drum is used which remains rotating throughout the following process, with the exception of required powder additions, necessary technical checks (e.g. pH, temperature, etc) and for draining processes.

(b) To the drum and the skins inside was added 25 wt % of water based on the limed weight of the skins at 28+/−1° C.

(c) The pH range of the aqueous liquor and the skins is adjusted to 7.0+/−0.2. This was measured using Phenol Red indicator (a yellow colour should be observed) to check the cross-section pH of the skins and a calibrated pH meter for the aqueous liquor.

(d) To the drum is then added 2.0 wt % of anhydrous sodium sulphate and 0.5 wt % sodium chloride based on the limed weight of the skins. This is run for a period of 30 minutes.

(e) To the drum is then added 6.0 wt % of colourless reactive tanning agent according to formula [2] and 0.5 wt % Acid Black 210 (powder form from generic supplier) based on the limed weight of the skins for a period of 100 minutes.

(f) A penetration check is made to ensure that the dye has adequately penetrated the cross-section of the skin.

(g) A total of 1.75 wt % Potassium Bicarbonate, 1.5 wt % Sodium Formate, 1 wt % anhydrous Sodium Sulphate and 1.5 wt % Potassium Carbonate based on the limed weight of the skins is added in six equal additions every 25 minutes to achieve a pH of 9.6 as measured by a calibrated pH meter.

(h) The drum continues to run for a period of 360 minutes, whilst periodically checking the pH of the liquor to ensure it does not fall below pH 9.2. During this time the drum naturally increases in temperature to give a final drum temperature of 34° C.

(i) The drum is then drained for 10 minutes.

(j) The leather is then washed with 125 wt % of water at 35° C. and 1.1 wt % Formic acid for a period of 30 minutes.

(k) The drum is then drained for 10 minutes.

(l) The leather is then washed with 175 wt % of water at 25° C. and 1.1 wt % Formic acid for a period of 30 minutes.

(m) The pH of the liquor is checked to ensure it is 5.0+/−0.2.

(n) 0.15% commercially available leather biocide (Preventol WB) is then added for a period of 120 minutes.

(o) The leather is then removed and aged ('horsed up') for a period of 36 hours prior to further standard leather processing.

The hydrothermal stability, as tested by the standard method of ISO 3380:2015 to irreversible shrinkage for specific example C was 78° C.

Colour fastness for Specific Example C was Greyscale Rating 3.5 to Water Contact and Greyscale Rating 2.5 to Perspiration Contact (both assessed to the cotton zone of the multifibre strip) on both the Grain and Fleshside.

The following specific examples D and E each illustrate a specific cross-linking (tanning) process (with and without simultaneous dyeing) on a specific collagenous substrate thereby using the cross-linking agent according to formula [2]. The wt % of cross-linking agent (and dye) mentioned in below examples are based upon the drained pickled weight of the collagenous substrates used and the processes described below start with material that has been previously pickled.

Specific Example D: Tanning Process on Spanish Source Goatskin With Sole Use of the Colourless Reactive Tanning Agent According to Formula (2)

(a) A rotating drum is used which remains rotating throughout the following process, with the exception of required powder additions, necessary technical checks (e.g. pH, temperature, etc), addition of the pickled skins and for draining processes.

(b) To the drum was added 100 wt % of water at 25+/−1° C., 6 wt % sodium chloride, 0.25 wt % EDTA and 0.5 wt % of non-ionic surfactant (100% active content such as Eusapon OC) as based on the pickle weight of the goatskins and the drum is rotated for a period of 15 minutes.

(c) To the drum is added the pickled goatskins, along with 4 wt % of Sodium Bicarbonate based on the pickle weight of the goatskins. This is run for a period of 120 minutes.

(d) The pH range of the liquor and the goatskins is checked to be 6.8+/−0.2. This is through using Bromothymol Blue indicator (a green colour should be observed) to check the cross-sectional pH of the goatskins and a calibrated pH meter to measure the pH of the aqueous liquor.

(e) The drum is then drained for 10 minutes.

(f) To the drum was added 250 wt % by weight of water at 30+/−1° C., as based on the pickle weight of the goatskins and the drum is rotated for a period of 20 minutes.

(g) The drum is then drained for 10 minutes.

(h) To the drum was added 250 wt % by weight of water at 30+/−1° C., as based on the pickle weight of the goatskins and the drum is rotated for a period of 20 minutes.

(i) The drum is then drained for 10 minutes.

(j) To the drum was added 250 wt % by weight of water at 30+/−1° C., as based on the pickle weight of the goatskins and the drum is rotated for a period of 20 minutes.

(k) The drum is then drained for 10 minutes.
(l) To the drum was added 45 wt % by weight of water at 28+/−1° C., as based on the pickle weight of the goatskins and the drum is rotated for a period of 15 minutes.
(m) The pH range of the liquor and the goatskins is checked once again to be 6.8+/−0.2. This is through using Bromothymol Blue indicator (a green colour should be observed) to check the cross-sectional pH of the goatskins and a calibrated pH meter to measure the pH of the aqueous liquor.
(n) To the drum is added 5 wt % of anhydrous sodium sulphate based on the pickled weight of the goatskins. This is run for a period of 15 minutes.
(o) To the drum is then added 9 wt % of colourless reactive tanning agent according to formula [2] based on the pickled weight of the goatskins for a period of 120 minutes.
(p) A total of 3.6 wt % Potassium Bicarbonate and 2.4 wt % Potassium Carbonate based on the pickled weight of the goatskins is then added in four equal additions every 40 minutes to achieve a pH of 9.4 as measured by a calibrated pH meter.
(q) The drum continues to run for a period of 400 minutes, whilst periodically checking the pH of the liquor to ensure it does not fall below pH 9.2. During this time the drum naturally increases in temperature due to internal friction and increases from 30° C. to 35° C.
(r) The drum is then drained for 10 minutes.
(s) The leather is then washed with 150 wt % water at 30° C. and 1.4 wt % Formic acid based on the pickled weight of the goatskins for a period of 30 minutes.
(t) The drum is then drained for 10 minutes.
(u) The leather is then washed with 150 wt % water at 30° C. and 1.25 wt % Formic acid based on the pickled weight of the goatskins for a period of 30 minutes.
(v) The drum is then drained for 10 minutes.
(w) The leather is then washed with 100 wt % water at 20° C. and 0.35 wt % Formic acid based on the pickled weight of the goatskins and 0.25 wt % commercially available leather biocide (Preventol WB) based on the pickled weight of the goatskins for a period of 60 minutes. The pH of the liquor is checked to ensure it is 4.9+/−0.2. The cross-section of the leather is checked with Bromocresol Green indicator solution and should be a green-blue colour.
(x) The leather is then removed and aged ('horsed up') for a period of 36 hours prior to further standard leather processing.

The hydrothermal stability, as tested by the standard method of ISO 3380:2015 to irreversible shrinkage for specific example D was 79° C.

Specific Example E: Tanning and Dyeing Process on Australian Kangaroo Skins With Combined Use of Colourless Reactive Tanning Agent According to Formula (2) and a Reactive Dye (a) A rotating drum is used which remains rotating throughout the following process, with the exception of required powder additions, necessary technical checks (e.g. pH, temperature, etc), addition of the pickled skins and for draining processes.
(b) To the drum was added 125 wt % of water at 23+/−1° C., 7 wt % sodium chloride, 0.3 wt % EDTA and 0.4 wt % of non-ionic surfactant (100% active content such as Eusapon OC) as based on the pickle weight of the kangaroo skins and the drum is rotated for a period of 15 minutes.
(c) To the drum is added the pickled kangaroo skins, along with 4.25 wt % of Sodium Bicarbonate and 0.5 wt % of Sodium Formate based on the pickle weight of the kangaroo skins. This is run for a period of 180 minutes.
(d) The pH range of the liquor and the kangaroo skins is checked to be 6.6+/−0.2. This is through using Bromocresol Purple indicator (a purple colour should be observed) to check the cross-sectional pH of the goatskins and a calibrated pH meter to measure the pH of the aqueous liquor.
(e) The drum is then drained for 10 minutes.
(f) To the drum was added 250 wt % of water at 30+/−1° C., as based on the pickle weight of the pickled kangaroo skins and the drum is rotated for a period of 15 minutes.
(g) The drum is then drained for 10 minutes.
(h) To the drum was added 200 wt % of water at 30+/−1° C., as based on the pickle weight of the kangaroo skins and the drum is rotated for a period of 20 minutes.
(i) The drum is then drained for 10 minutes.
(j) To the drum was added 200 wt % of water at 30+/−1° C., as based on the pickle weight of the kangaroo skins and the drum is rotated for a period of 20 minutes.
(k) The drum is then drained for 10 minutes.
(l) To the drum was added 40 wt % of water at 30+/−1° C., as based on the pickle weight of the kangaroo skins and the drum is rotated for a period of 20 minutes.
(m) The pH range of the liquor and the skins is adjusted to 6.7+/−0.2. This was measured through use of Bromocresol Purple indicator (a purple colour should be observed) to check the cross-section pH of the skins and a calibrated pH meter for the aqueous liquor.
(n) To the drum is added 5.0 wt % of anhydrous sodium sulphate based on the pickled weight of the kangaroo skins. This is run for a period of 25 minutes.
(o) To the drum is then added 3.5 wt % of colourless reactive tanning agent according to formula (2) and 5 wt % of reactive dye based on the pickled weight of the kangaroo skins over a period of 120 minutes.
(p) A penetration check is made to ensure that the dye has adequately penetrated the cross-section of the skin.
(q) A total of 1.95 wt % Sodium Bicarbonate, 0.5 wt % Sodium Formate and 1.75 wt % Sodium Carbonate (based on the pickled weight of the kangaroo skins) is added in five equal additions every 20 minutes to achieve a pH of 9.5 as measured by a calibrated pH meter.
(r) The drum continues to run for a period of 420 minutes, whilst periodically checking the pH of the liquor to ensure it does not fall below pH 9.2. During this time the drum is programmed to increase in temperature at a gradient of 1.0° C. every 60 minutes to give a final drum temperature of 36° C.
(s) The drum is then drained for 10 minutes.
(t) The leather is then washed with 150 wt % water based on the pickled weight of the kangaroo skins at 33° C. and 1.5 wt % Formic acid based on the pickled weight of the kangaroo skins for a period of 30 minutes.
(u) The drum is then drained for 10 minutes.
(v) The leather is then washed with 200 wt % water based on the pickled weight of the kangaroo skins at 30° C. and 1.25 wt % Formic acid based on the pickled weight of the skins for a period of 30 minutes.
(w) The drum is then drained for 10 minutes.

(x) The leather is then washed with 100 wt % water at 25° C. and 0.5 wt % Formic acid and 0.25 wt % commercially available leather biocide (Preventol WB) based on the pickled weight of the kangaroo skins for a period of 75 minutes. The pH of the liquor is checked to ensure it is 4.8+/−0.2.

(y) The leather is then removed and aged ('horsed up') for a period of 24 hours prior to further standard leather processing.

Figure 3:
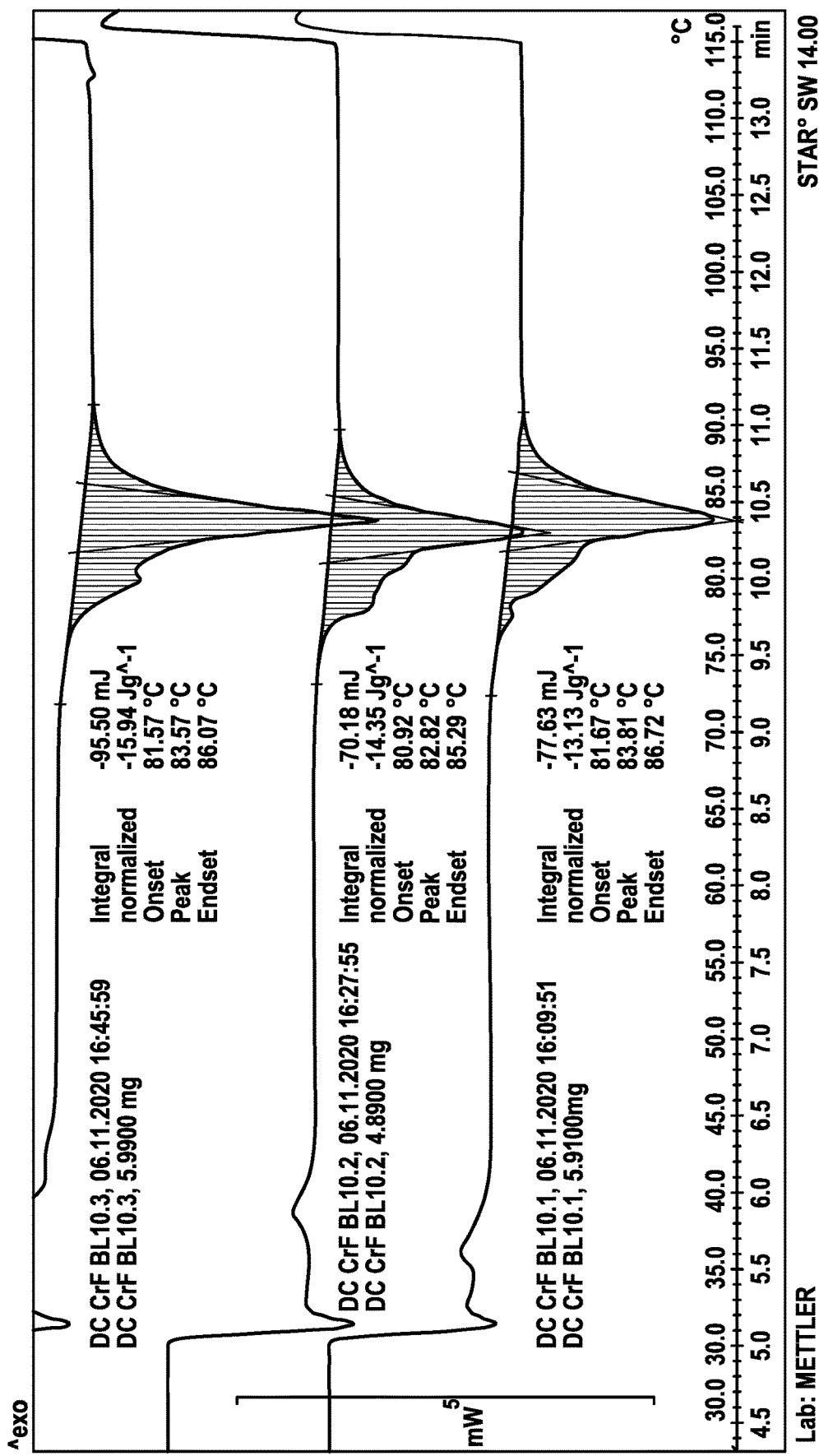
FIG. 3 shows Differential Scanning calorimetry (DSC) graphs (3 repeats) illustrating the hydrothermal stability for specific example E according to the invention (the 'Onset' temperature is the value taken as the hydrothermal stability).

FIG. 3 shows Differential Scanning calorimetry (DSC) graphs (3 repeats) illustrating the hydrothermal stability for specific example E according to the invention (the 'Onset' temperature is the value taken as the hydrothermal stability).

Colour fastness for Specific Example E was Greyscale Rating 5 to Water Contact and Greyscale Rating 4.5 to Perspiration Contact (both assessed to the cotton zone of the multifibre strip) on both the Grain and Fleshside.

Specific Example F and Comparative Example 1:
Tanning Processes on UK Source Cow Hide
Respectively With Sole Use of a Reactive Tanning
Agent of Formula (A) and With the Composition 2
Described in WO 2010/130311

Two pieces of limed split bovine hide were used respectively for Specific Example F and Comparative Example 1 and said pieces of hide were taken adjacent to each other from the same hide to minimize any variation during the tanning process.

Specific Example F: Tanning Process According to
Specific Example A With Sole Use of the
Colourless Reactive Tanning Agent According to
Formula (2)

The here above-described hide was tanned according to the process described in Specific Example A and using 5.7 wt % of reactive tanning agent, same conditions of pH and time as disclosed in the Specific Example A with the reactive agent according to a formula (2).

Comparative Example 1: Tanning Process
According to Application Example A With the
Composition 2, Both Described in WO
2010/130311

The here above-described hide was tanned according to the process described in Application Example A in WO 2010/130311 by using the composition 2 disclosed in WO 2010/130311. In the Application Example A in WO 2010/130311, 10% of composition 2 is using in the tanning process, and this is equal in terms of moles added to that of 5.7 wt % of reactive tanning agent of formula (2) according to Specific Example F.

Figure 4:
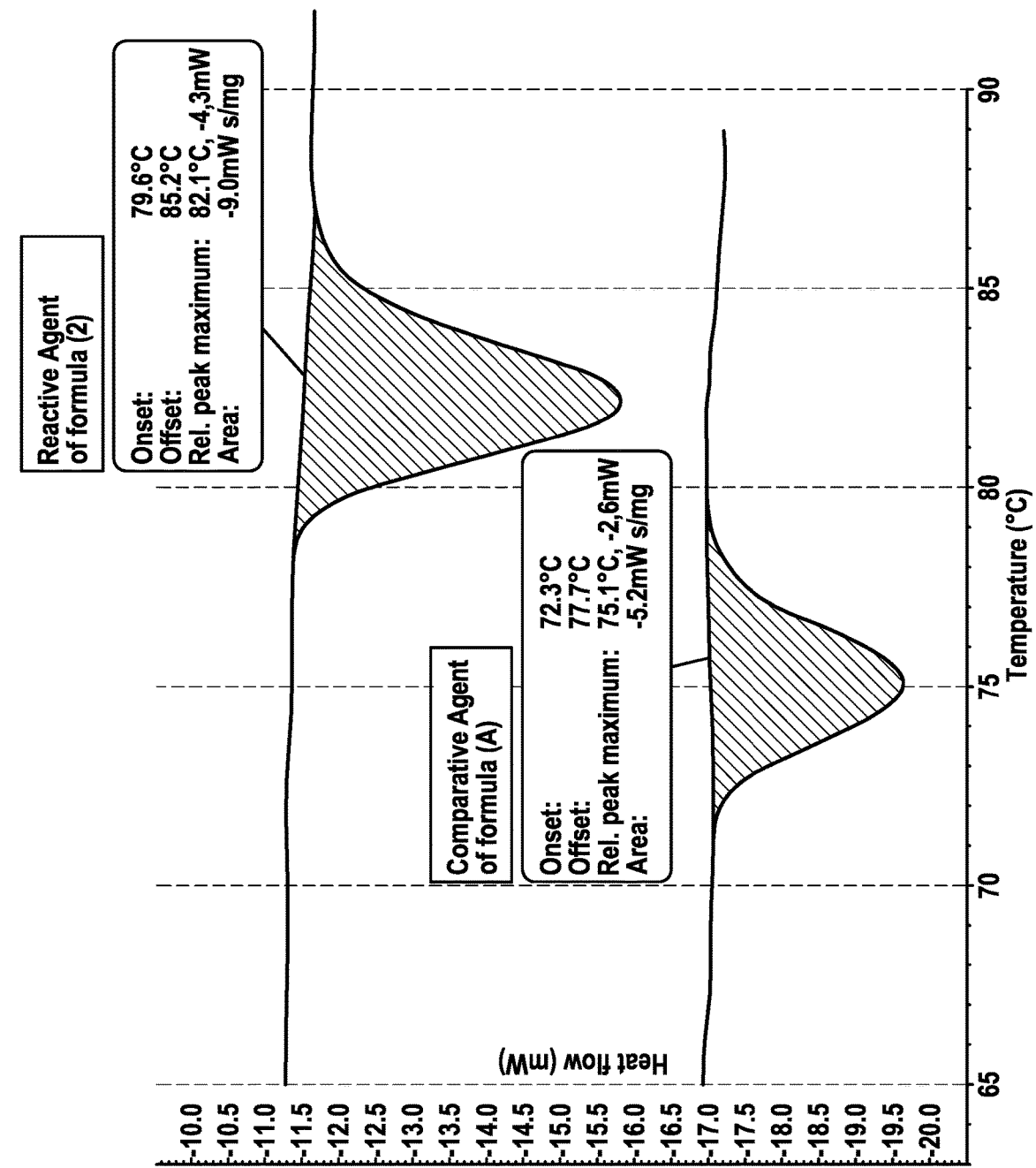
FIG. 4 shows Differential Scanning calorimetry (DSC) graphs illustrating the hydrothermal stabilities for specific example F according to the invention and for a comparative example 1 (the 'Onset' temperature is the value taken as the hydrothermal stability).

FIG. 4 shows Differential Scanning calorimetry (DSC) graphs illustrating the hydrothermal stabilities for specific example F according to the invention and for the comparative example 1 (the 'Onset' temperature is the value taken as the hydrothermal stability).

FIG. 4 demonstrates that the hydrothermal stability of the hide tanned with the reactive agent according to the invention is 79.6° C. while the hydrothermal stability of the hide tanned with the reactive agent not according to the invention is only 72.3° C.

Specific Example G: Measurement of the
Hydrothermal Stability of Tanned Hide According
to Specific Example F After 4 Months of Ageing A sample of the tanned hide piece obtained in specific Example F was taken and placed into a container, immersing the sample in deionized water. The container was then sealed and stored at room temperature for a period of 4 months.

The sample was then removed from the sealed container and tested for hydrothermal stability using DSC analysis test methodologies as previously described.

Figure 5:
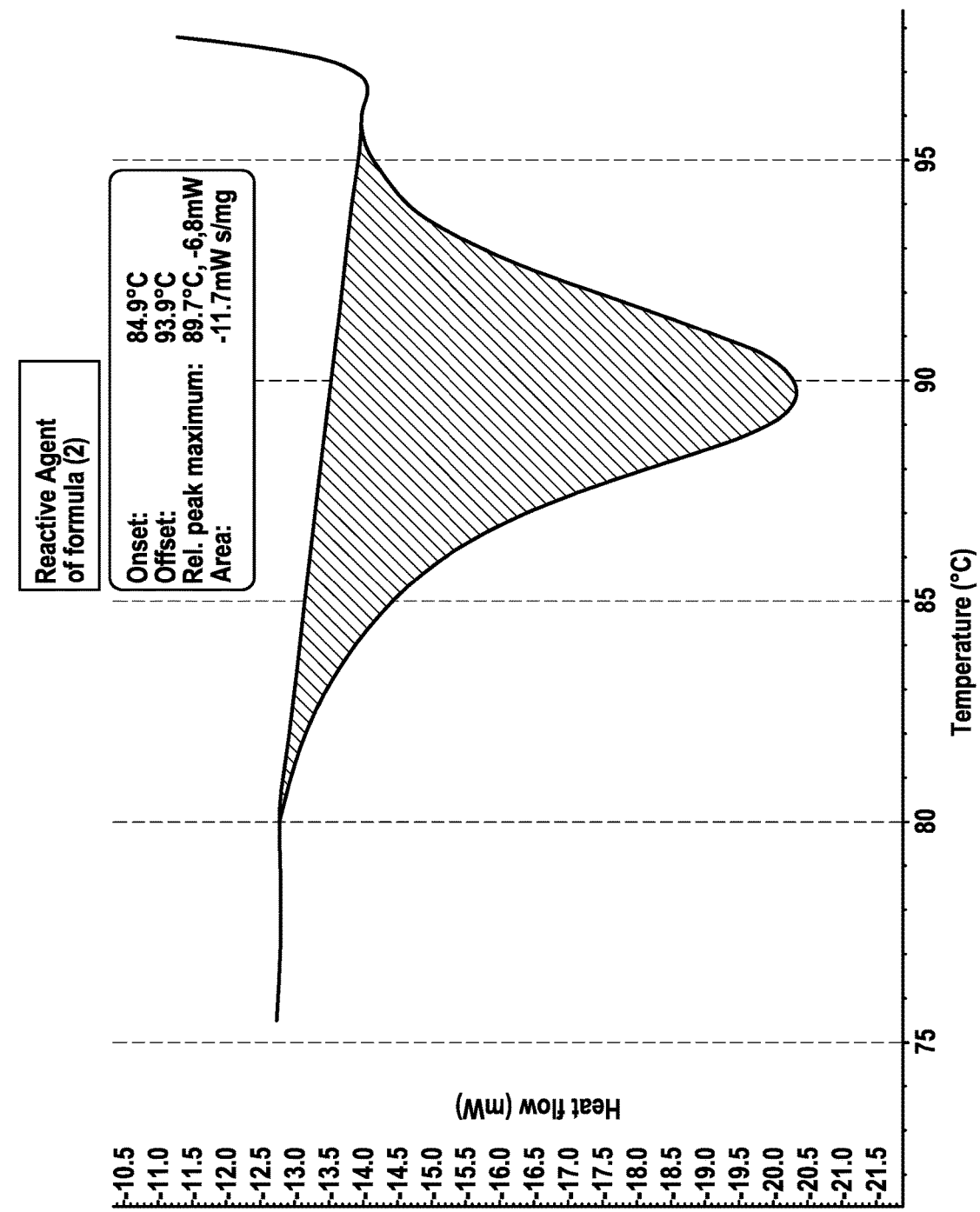
FIG. 5 shows Differential Scanning calorimetry (DSC) graphs illustrating the hydrothermal stability for specific example G according to the invention (the 'Onset' temperature is the value taken as the hydrothermal stability).

FIG. 5 shows Differential Scanning calorimetry (DSC) graph illustrating the hydrothermal stability for specific example G according to the invention (the 'Onset' temperature is the value taken as the hydrothermal stability).

FIG. 5 demonstrates that the hydrothermal stability of the hide tanned with the reactive tanning agent according to the invention increases from 79.6° C. to 84.9° C. after the ageing process. This result signifies not only that the cross-linking/tanning effect is permanent but also that it improves over time.

The invention claimed is:

1. A reactive colourless protein cross-linking agent for the cross-linking of protein-based substrates having amine and optionally OH functionality, said cross-linking agent comprising a compound according to formula [1]:

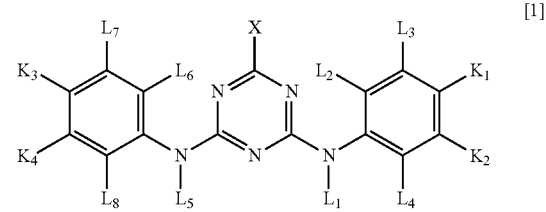

wherein
$L_1$ and $L_5$ are each independently from each other selected from H or $C_1$-$C_4$ alkyl, and $L_2$, $L_3$, $L_4$, $L_6$, $L_7$ and $L_8$ are each independently from each other selected from H, $C_1$-$C_4$ alkyl, $SO_3H$, and $OL_{22}$ wherein $L_{22}$ is selected from H and $C_1$-$C_4$ alkyl, and X is selected from Cl, F and nicotinic acid, and $K_1$, $K_2$, $K_3$ and $K_4$ are each independently from each other selected from —H and protein reactive radicals, and wherein the protein-based substrates are selected from collagen containing fibrous material, gelatin, fibroin, elastin and soy (soyabean).

2. The reactive colourless protein cross-linking agent according to claim 1, wherein the protein reactive radicals are selected from

—$SO_2$—Y,

—NH—$(CH_2)_{2-3}$—$SO_2$—Y,

—NH—CO—$(CH_2)_{2-3}$—$SO_2$—Y,

—NH—$(CH_2)_2$—O—$(CH_2)_2$—$SO_2$—Y,

—NH—CO—CHW—$CH_2$—W, and

—NH—CO—C(W)=$CH_2$ wherein Y is selected from —$CH_2$—$CH_2$—U and —CH=$CH_2$, and U and W are independently from each other a group removable under alkaline conditions.

3. The reactive colourless protein cross-linking agent according to claim 2, wherein U and W are independently from each other selected from
—Cl, —Br, or —F,
—OSO₃H,
—SO₃H,
—OCO—CH₃,
—OPO₃H₂,
—OCO—C₆H₅,
—OSO₂-C₁-C₄alkyl, and
—OSO₂N(C₁-C₄alkyl)₂.

4. The reactive colourless protein cross-linking agent according to claim 3, wherein U and W are independently from each other selected from —Cl, —OSO₃H, —SO₃H, —OCO—CH₃, —OCO—C₆H₅ and —OPO₃H₂.

5. The reactive colourless protein cross-linking agent according to claim 1, wherein $K_1$, $K_2$, $K_3$ and $K_4$ are each independently from each other selected from H, SO₂—CH=CH₂ and —SO₂—CH₂—CH₂—U and wherein U is a group removable under alkaline conditions.

6. The reactive colourless protein cross-linking agent according to claim 1, wherein the cross-linking agent is selected from compounds according to formula [2], [3], [4], [5], [6], [7], [8], [9] and [10]:

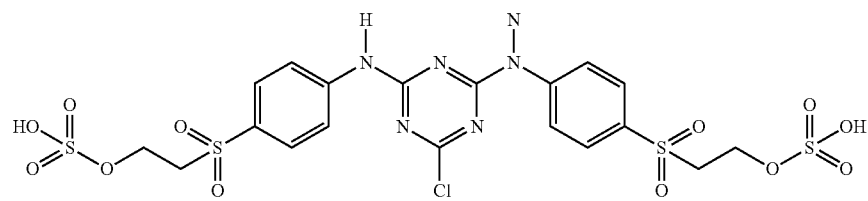

[2]

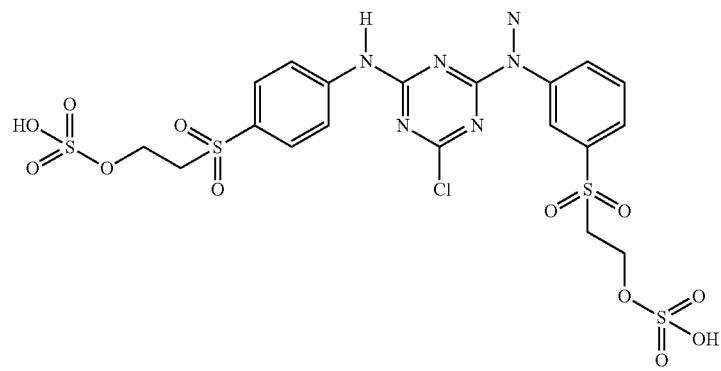

[3]

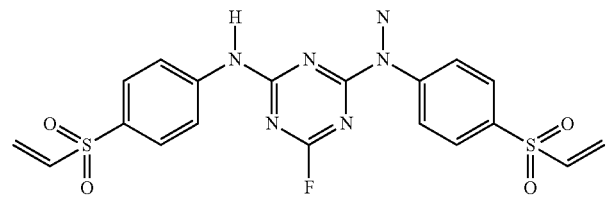

[4]

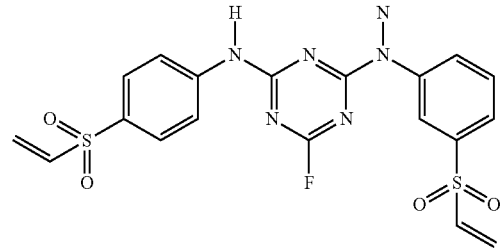

[5]

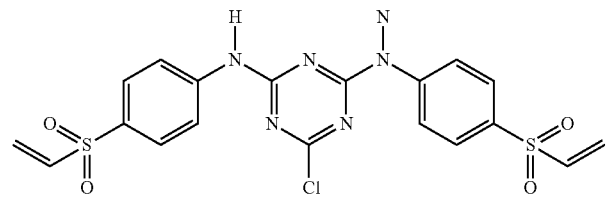

[6]

-continued

[7]
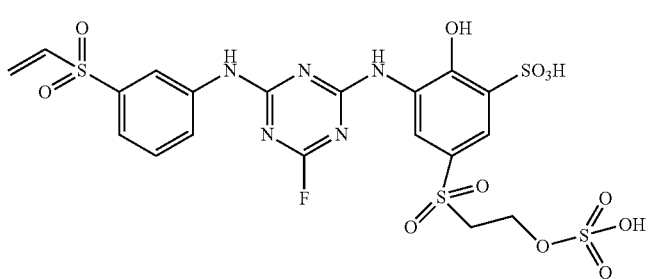

[8]
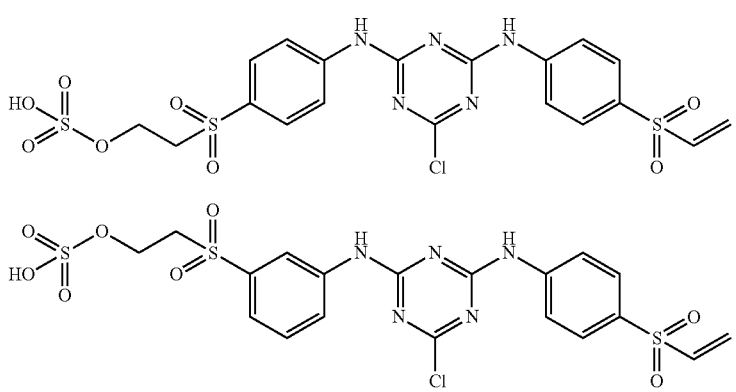

[9]
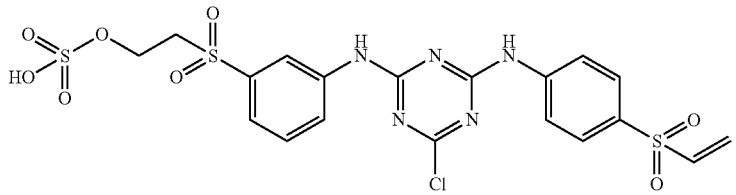

[10]
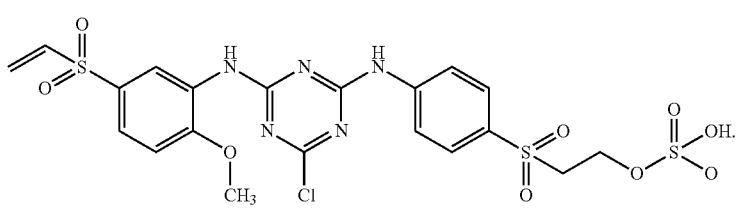

7. A composition comprising the reactive colourless protein cross-linking agent according to claim 1 and at least one dye.

8. The composition according to claim 7, wherein the dye is a reactive dye comprising a mono, bi, tri and/or poly functional reactive dye having at least one protein reactive radical.

9. The composition according to claim 8, wherein the at least one reactive dye is selected from compounds according to formula [20] and [21]

$$A_1\text{---}(Z_1)_{2\text{-}3}, \text{ and} \quad [20]$$

[21]
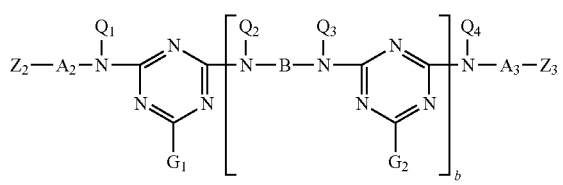

wherein
$A_1$, $A_2$ and $A_3$ are each independently of the others a radical of a monoazo, polyazo, metal-complexed azo, anthraquinone, phthalocyanine, formazan or dioxazine chromophore having at least one sulfo group,
B is an organic bridge member,
$Q_1$, $Q_2$, $Q_3$ and $Q_4$ are each independently of the others hydrogen or unsubstituted or substituted $C_1$-$C_4$alkyl,
$G_1$ and $G_2$ are halogen, 3-carboxypyridin-1-yl or 3-carbamoylpyridin-1-yl,
$(Z_1)_{2\text{-}3}$ is 2 to 3 identical or different protein reactive radicals,
$Z_2$ and $Z_3$ are each independently of the other identical or different protein reactive radicals, and
b is the number 0 or 1.

10. The composition according to claim 9, wherein the protein reactive radicals $Z_1$, $Z_2$ and $Z_3$ are each independently of the others a radical of the formula

| | |
|---|---|
| —SO$_2$—Y | (3a), |
| —NH—CO—(CH$_2$)$_r$—SO$_2$—Y | (3b), |
| —CONR$_2$—(CH$_2$)$_m$—SO$_2$—Y | (3c), |
| —NH—CO—CH(Hal)—CH$_2$—Hal | (3d), |
| —NH—CO—C(Hal)=CH$_2$ | (3e), |

(3f)
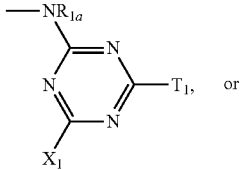
or

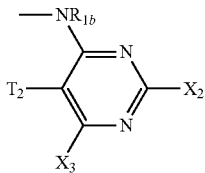
(3g)

wherein
Hal is chlorine or bromine;
$X_1$ is halogen, 3-carboxypyridin-1-yl or 3-carbamoylpyridin-1-yl;
$T_1$ independently has the meaning of $X_1$, or is a substituent which is not protein reactive, or is a protein reactive radical of the formula:

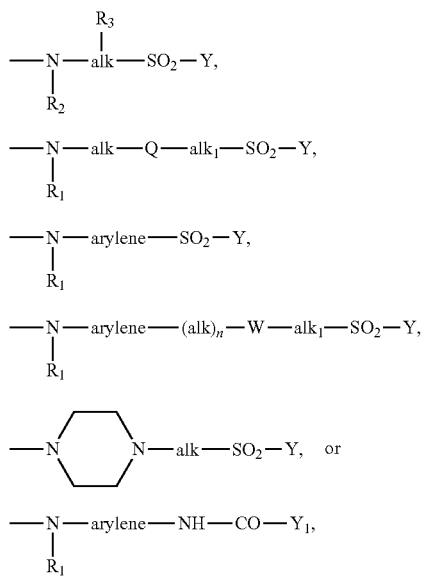

(4a)

(4b)

(4c)

(4d)

(4e)

(4f)

wherein
$R_1$, $R_{1a}$ and $R_{1b}$ independently of one another are each hydrogen or $C_1$-$C_4$alkyl,
$R_2$ is hydrogen, $C_1$-$C_4$alkyl which is unsubstituted or substituted by hydroxyl, sulfo, sulfato, carboxyl or cyano or a radical

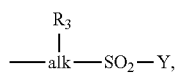

$R_3$ is hydrogen, hydroxyl, sulfo, sulfato, carboxyl, cyano, halogen, $C_1$-$C_4$alkoxycarbonyl, $C_1$-$C_4$alkanoyloxy, carbamoyl or the group —$SO_2$—Y,
alk and $alk_1$ independently of one another are linear or branched $C_1$-$C_6$alkylene,
arylene is a phenylene or naphthylene radical which is unsubstituted or substituted by sulfo, carboxyl, $C_1$-$C_4$alkyl, $C_1$-$C_4$alkoxy or halogen,
Q is a radical —O— or —$NR_1$—, in which $R_1$ is as defined above, W is a group —$SO_2$—$NR_2$—, —$CONR_2$— or —$NR_2CO$—, in which $R_2$ is as defined above,
Y is vinyl or a radical —$CH_2$—$CH_2$—U and U is a group which can be split off under alkaline conditions,
$Y_1$ is a group —CH(Hal)—$CH_2$—Hal or —C(Hal)=$CH_2$ and Hal is chlorine or bromine and
l and m independently of one another are an integer from 1 to 6 and n is the number 0 or 1;
and
$X_2$ is halogen or $C_1$-$C_4$alkylsulfonyl;
$X_3$ is halogen or $C_1$-$C_4$alkyl; and
$T_2$ is hydrogen, cyano or halogen.

11. The composition according to claim 7, wherein the dye is an acid dye comprising acidic groups.

12. A process for cross-linking a protein-based substrate having amine and optionally OH functionality, said process comprising:
placing the protein-based substrate in a liquid medium, in a processing vessel, at temperature in the range 10° C. to 50° C.,
adding the reactive cross-linking agent according to claim 1 to the liquid medium in an amount in the range between 1 wt % and 40 wt % based on the dry weight of the protein-based substrate,
letting the reactive cross-linking agent penetrate for a period of time into the protein-based substrate,
adjusting the pH of the liquid medium in order for the cross-linking agent to react with the protein reactive groups in the protein-based substrate to complete the cross-linking reaction, and
rinsing/washing of the cross-linked substrate.

13. A process for simultaneously cross-linking and dyeing a protein-based substrate having amine and optionally OH functionality, said process comprising:
placing the protein-based substrate in a liquid medium, in a processing vessel, at temperature in the range 10° C. to 50° C.,
adding the reactive cross-linking agent according to claim 1 and a reactive dye to the aqueous liquid in an amount such that the amount of cross-linking agent is 1 wt % to 39 wt % and the amount of reactive dye is 1 wt % to 39 wt % based on the dry weight of the protein-based substrate,
letting the reactive cross-linking agent and reactive dye penetrate for a period of time into the protein-based substrate,
adjusting the pH of the liquid medium in order for the reactive cross-linking agent and reactive dye to react with the protein reactive groups in the protein-based substrate to complete the cross-linking and dyeing reaction, and
rinsing/washing of the cross-linked and dyed substrate.

14. A cross-linked protein-based substrate obtained by the process according to claim 12.

15. A cross-linked and dyed protein-based substrate obtained by the process according to claim 13.

16. The cross-linked and dyed protein-based substrate according to claim 14, wherein the substrate is selected from collagen containing fibrous material, gelatin, fibroin, elastin and soy (soyabean).

17. The cross-linked and dyed protein-based substrate according to claim 15, wherein the substrate is selected from collagen containing fibrous material, gelatin, fibroin, elastin and soy (soyabean).

* * * * *